(12) United States Patent
Kita et al.

(10) Patent No.: US 11,248,226 B2
(45) Date of Patent: Feb. 15, 2022

(54) RIBOSOME DISPLAY COMPLEX AND PRODUCTION METHOD THEREFOR

(71) Applicant: KANEKA CORPORATION, Osaka (JP)

(72) Inventors: Hiroshi Kita, Hyogo (JP); Toshihiro Shikakura, Hyogo (JP); Hirofumi Maeda, Hyogo (JP); Keishi Takatsu, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 525 days.

(21) Appl. No.: 16/213,454

(22) Filed: Dec. 7, 2018

(65) Prior Publication Data

US 2019/0169600 A1 Jun. 6, 2019

Related U.S. Application Data

(63) Continuation of application No. PCT/JP2017/021038, filed on Jun. 6, 2017.

(30) Foreign Application Priority Data

Jun. 7, 2016 (JP) .............................. JP2016-113935

(51) Int. Cl.
*C12N 15/10* (2006.01)
*C12P 21/00* (2006.01)
(Continued)

(52) U.S. Cl.
CPC ............ *C12N 15/1041* (2013.01); *C07K 2/00* (2013.01); *C12N 15/09* (2013.01); *C12P 21/00* (2013.01); *C40B 40/10* (2013.01)

(58) Field of Classification Search
CPC .................................................. C12N 15/1041
See application file for complete search history.

(56) References Cited

U.S. PATENT DOCUMENTS

2010/0317547 A1 12/2010 Gregory et al.
2012/0101253 A1 4/2012 Heinis et al.
(Continued)

FOREIGN PATENT DOCUMENTS

JP 2007-137690 A 6/2007
JP 2011-514803 A 5/2011
(Continued)

OTHER PUBLICATIONS

H. Leemhuis et al., "New genotype-phenotype linkages for directed evolution of functional proteins", Current Opinion in Structural Biology 2005, vol. 15, pp. 472-478 (7 page).
(Continued)

*Primary Examiner* — Jeremy C Flinders
(74) *Attorney, Agent, or Firm* — Osha Bergman Watanabe & Burton LLP

(57) ABSTRACT

A method for producing a ribosome display complex includes obtaining a ribosome complex including an unmodified polypeptide chain, an mRNA molecule and a ribosome by initiating translation of the mRNA molecule in a cell-free peptide synthesis system including the ribosome, and modifying the unmodified polypeptide chain by reacting a side chain reactive functional group in the unmodified polypeptide chain with a modifying reagent to produce a ribosome display complex including a modified polypeptide chain, the mRNA molecule and the ribosome. The unmodified polypeptide chain includes at least one reactive amino acid residue selected from the group consisting of a cysteine residue, a lysine residue, a histidine residue and a tryptophan residue. The at least one reactive amino acid residue includes the side chain reactive functional group, and the mRNA molecule includes a base sequence encoding an amino acid sequence of the polypeptide chain.

24 Claims, 14 Drawing Sheets

Specification includes a Sequence Listing.

(51) Int. Cl.
  *C12N 15/09* (2006.01)
  *C07K 2/00* (2006.01)
  *C40B 40/10* (2006.01)

(56) References Cited

U.S. PATENT DOCUMENTS

| | | |
|---|---|---|
| 2012/0101256 A1 | 4/2012 | Winter et al. |
| 2012/0142541 A1 | 6/2012 | Winter et al. |
| 2012/0172235 A1 | 7/2012 | Winter et al. |
| 2014/0163201 A1 | 6/2014 | Winter et al. |
| 2014/0187757 A1 | 7/2014 | Winter et al. |
| 2015/0166988 A1 | 6/2015 | Winter et al. |
| 2016/0046928 A1 | 2/2016 | Winter et al. |
| 2016/0060620 A1 | 3/2016 | Stafford et al. |
| 2017/0067045 A1 | 3/2017 | Winter et al. |
| 2018/0142232 A1 | 5/2018 | Stafford et al. |

FOREIGN PATENT DOCUMENTS

| | | |
|---|---|---|
| JP | 2013-518558 A | 5/2013 |
| JP | 2013-526830 A | 6/2013 |
| WO | 2014176439 A1 | 10/2014 |

OTHER PUBLICATIONS

D. Lipovsek et al., "In-vitro protein evolution by ribosome display and mRNA display", Journal of Immunological Methods, 2004, vol. 290, pp. 51-67 (17 pages).

H. M. E. Azzazy et al., "Phage display technology: clinical applications and recent innovations", Clinical Biochemistry, 2002, vol. 35, pp. 425-445 (21 pages).

H. L. Perez et al., "Antibody-drug conjugates: current status and future directions", Drug Discovery Today, Jul. 2014, vol. 19, No. 7, pp. 869-881 (13 pages).

S. C. Alley et al., "Antibody-drug conjugates: targeted drug delivery for cancer", Current Opinion in Chemical Biology, 2010, vol. 14, pp. 529-537 (9 pages).

C. Heinis et al., "Phage-encoded combinatorial chemical libraries based on bicyclic peptides", Nature Chemical Biology, Jul. 2009, vol. 5, No. 7, pp. 502-507 (6 pages).

I. R. Rebollo et al., "Phage selection of bicyclic peptides", Methods, 2013, vol. 60, pp. 46-54 (9 pages).

T. Kawakami et al., "Messenger RNA—Programmed Incorporation of Multiple N-Methyl-Amino Acids into Linear and Cyclic Peptides", Chemistry & Biology, Jan. 2008, vol. 15, No. 1, pp. 32-42 (11 pages).

K. Josephson et al., "mRNA display: from basic principles to macrocycle drug discovery", Drug Discovery Today, Apr. 2014, vol. 19, No. 4, pp. 388-399 (12 pages).

K. Fukunaga et al., "Construction of a crown ether-like supramolecular library by conjugation of genetically-encoded peptide linkers displayed on bacteriophage T7", Chemical Communications, 2014, vol. 50, pp. 3921-3923 (4 pages).

International Search Report issued in International Application No. PCT/JP2017/021038, dated Sep. 5, 2017 (2 pages).

Written Opinion issued in International Application No. PCT/JP2017/021038, dated Sep. 5, 2017 (5 pages).

A. Rothe et al., "Ribosome display for improved biotherapeutic molecules", Expert Opinion on Biological Therapy, Ashley Publications; vol. 6, No. 2, pp. 177-187; Feb. 1, 2006 (11 pages).

R. Gan et al., "Evolution of Translation Initiation Sequences Using In Vitro Yeast Ribosome Display", Biotechnology and Bioengineering; vol. 113, No. 8, pp. 1777-1786; Jan. 12, 2016 (10 pages).

C. Zahnd et al., "Ribosome display: selecting and evolving proteins in vitro that specifically bind to a target", Nature Methods; vol. 4, No. 3, pp. 269-279; Mar. 1, 2007 (11 pages).

D. R. Southworth et al., "EFG-independent Translocation of the mRNA:tRNA Complex is Promoted by Modification of the Ribosome with Thiol-specific Reagents", Journal of Molecular Biology, Academic Press; vol. 324, No. 4, pp. 611-623; Dec. 6, 2002 (13 pages).

S. Fujita et al., "Novel Approach for Linking Genotype to Phenotype in Vitro by Exploiting an Extremely Strong Interaction between RNA and Protein", Journal of Medicinal Chemistry; vol. 45, No. 8, pp. 1598-1606; Apr. 1, 2002 (9 pages).

Extended European Search Report issued in corresponding European Application No. 17810332.1, dated Dec. 2, 2019 (11 pages).

```
                              SEQUENCE LISTING

<160> NUMBER OF SEQ ID NOS: 14

<210> SEQ ID NO 1
<211> LENGTH: 707
<212> TYPE: DNA
<213> ORGANISM: Artificial Sequence
<220> FEATURE:
<221> NAME/KEY: CDS
<222> LOCATION: 201..230
<223> OTHER INFORMATION: n stands for any base and k stands for g or t
<220> FEATURE:
<223> OTHER INFORMATION: Synthetic DNA

<400> SEQUENCE: 1
aagcttggta ccgagctcgg atccactagt aacggccgcc agtgtgctgg aattcgccct      60
tgaaattaat acgactcact atagggagac cacaacggtt tccctctaga ataattttg     120 tttaactta  agaaggagat ataccaatgg actataaaga tgacgatgac aaaggtcacc    180
atcatcacca tcacggttgc nnknnknnkn nknnknnknn knnknnknnk tgcggcgaaa    240
acctgtattt ccagggcggt gcaggtggca gcggaggtgg tggcagcgga ggtgaatatc    300
aaggccaatc gtctgaccag aagcaagctg aagaggcgg  agcgaaagcg gcggcagatg    360
ctaaagcgaa ggccgaagca gatgctaaag ctgcggaaga agcagcgaag aaagcggctg    420
cagacgcaaa gaaaaaagca gaagcagaag ccgccaaagc cgcagccgaa gcgcagaaaa    480
aagccgaggc agccgctgcg gcactgaaga agaaagcgga agcggcagaa gcagctgcag    540
ctgaagcaag aaagaaagcg gcaactgaag ctgctgaaaa agccaaagca gaagctgaga    600
agaaagcggc tgctgaaaag gctgcagctg ataaggcaaa attcagcacg cccgtctgga    660
taagccaggc gcaaggcatc cgtgctggcc ctcaacgcct cacctaa                  707

<210> SEQ ID NO 2
<211> LENGTH: 186
<212> TYPE: PRT
<213> ORGANISM: Artificial Sequence
<220> FEATURE:
<221> NAME/KEY: MISC_FEATURE
<222> LOCATION: 19..28
<223> OTHER INFORMATION: Xaa stands for any amino acid
<220> FEATURE:
<223> OTHER INFORMATION: Designed peptide for a library

<400> SEQUENCE: 2

Met Asp Tyr Lys Asp Asp Asp Lys Gly His His His His His
1               5                   10                  15

Gly Cys Xaa Xaa Xaa Xaa Xaa Xaa Xaa Xaa Cys Gly Glu Asn
            20                  25                  30

Leu Tyr Phe Gln Gly Gly Ala Gly Gly Ser Gly Gly Gly Ser Gly
            35                  40                  45

Gly Glu Tyr Gln Gly Gln Ser Ser Asp Gln Lys Gln Ala Glu Ala
        50                  55                  60

Ala Ala Lys Ala Ala Ala Asp Ala Lys Ala Lys Ala Glu Ala Asp Ala
65                  70                  75                  80

Lys Ala Ala Glu Glu Ala Ala Lys Lys Ala Ala Ala Asp Ala Lys Lys
                85                  90                  95
```

```
Lys Ala Glu Ala Glu Ala Lys Ala Ala Glu Ala Gln Lys Lys
            100                 105                 110

Ala Glu Ala Ala Ala Ala Leu Lys Lys Ala Glu Ala Glu
    115                 120                 125

Ala Ala Ala Ala Glu Ala Arg Lys Lys Ala Ala Thr Glu Ala Ala Glu
130                 135                 140

Lys Ala Lys Ala Glu Ala Glu Lys Lys Ala Ala Glu Lys Ala Ala
145                 150                 155                 160

Ala Asp Lys Ala Lys Phe Ser Thr Pro Val Trp Ile Ser Gln Ala Gln
                165                 170                 175

Gly Ile Arg Ala Gly Pro Gln Arg Leu Thr
            180                 185

<210> SEQ ID NO 3
<211> LENGTH: 637
<212> TYPE: RNA
<213> ORGANISM: Artificial Sequence
<220> FEATURE:
<221> NAME/KEY: CDS
<222> LOCATION: 117..146
<223> OTHER INFORMATION: n stands for any base and k stands for g or u
<220> FEATURE:
<223> OTHER INFORMATION: Synthetic RNA

<400> SEQUENCE: 3
gggagaccac aacgguuucc cucuagaaau aauuuuguuu aacuuuaaga ggagauauac     60
caauggacua uaaagaugac gaugacaaag gucaccauca ucaccaucac gguugcnnkn   120
nknnknnknn knnknnknnk nnknnkugcg gcgaaaaccu guauuccag ggcggugcag    180 guggcagcgg agguggugg cagcggaggug aauaucaagg ccaaucgucu gaccagaagc   240
aagcugaaga ggcggcagcg aaagcggcgg cagaugcuaa agcgaaggcc gaagcagaug   300
cuaaagcugc ggaagaagca gcgaagaaag cggcugcaga cgcaaagaaa aaagcagaag   360
cagaagccgc caaagccgca gccgaagcgc agaaaaaagc cgaggcagcc gcugcggcac   420
ugaagaagaa agcggaagcg gcagaagcag cugcagcuga agcaagaaag aaagcggcaa   480
cugaagcugc ugaaaaagcc aaagcagaag cugagaagaa agcggcugcu gaaaaggcug   540
cagcugauaa ggcaaaauuc agcacgcccg ucuggauaag ccaggcgcaa ggcauccgug   600
cuggcccuca acgccucacc uaaugaauaa cuaaucc                            637

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
caaaggtcac catcatcacc atcacggttg c                                   31

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
tgcaccgccc tggaaataca ggttttcgcc gca                                 33
```

```
<210> SEQ ID NO 6
<211> LENGTH: 200
<212> TYPE: DNA
<213> ORGANISM: Artificial Sequence
<220> FEATURE:
<223> OTHER INFORMATION: 5' fragment

<400> SEQUENCE: 6
aagcttggta ccgagctcgg atccactagt aacggccgcc agtgtgctgg aattcgccct    60
tgaaattaat acgactcact atagggagac cacaacggtt ccctctaga aataattttg   120 tttaacttta agaaggagat ataccaatgg actataaaga tgacgatgac aaaggtcacc   180
atcatcacca tcacggttgc                                               200

<210> SEQ ID NO 7
<211> LENGTH: 491
<212> TYPE: DNA
<213> ORGANISM: Artificial Sequence
<220> FEATURE:
<223> OTHER INFORMATION: 3' fragment

<400> SEQUENCE: 7
tgcggcgaaa acctgtattt ccagggcggt gcaggtggca gcggaggtgg tggcagcgga    60
ggtgaatatc aaggccaatc gtctgaccag aagcaagctg aagaggcggc agcgaaagcg   120
gcggcagatg ctaaagcgaa ggccgaagca gatgctaaag ctgcggaaga agcagcgaag   180
aaagcggctg cagacgcaaa gaaaaaagca gaagcagaag ccgccaaagc cgcagccgaa   240
gcgcagaaaa agccgaggc agccgctgcg gcactgaaga gaaagcgga agcggcagaa   300 gcagctgcag ctgaagcaag aaagaaagcg gcaactgaag ctgctgaaaa agccaaagca   360
gaagctgaga gaaagcggc tgctgaaaag gctgcagctg ataaggcaaa attcagcacg   420
cccgtctgga taagccaggc gcaaggcatc cgtgctggcc ctcaacgcct cacctaatga   480
ataactaatc c                                                        491

<210> SEQ ID NO 8
<211> LENGTH: 661
<212> TYPE: RNA
<213> ORGANISM: Artificial Sequence
<220> FEATURE:
<223> OTHER INFORMATION: Designed RNA to code a peptide having affinity
      for HSP90

<400> SEQUENCE: 8
gggagaccac aacgguuucc cucuagaaau aauuuuguuu aacuuuaaga aggagauaua    60
ccaauggacu auaaagauga cgaugacaaa ggucaccauc auccauca cgguugcaag   120 cgucugcggg ggccauggga guggcugagg ugcggcgaaa accuguauuu ccagggcggu   180
gcagguggca gcggaggugg uggcagcgga ggugaauauc aaggccaauc gucugaccag   240
aagcaagcug aagaggcggc agcgaaagcg gcggcagaug cuaaagcgaa ggccgaagca   300
gaugcuaaag cugcggaaga agcagcgaag aaagcggcug cagacgcaaa gaaaaaagca   360
gaagcagaag ccgccaaagc cgcagccgaa gcgcagaaaa agccgaggc agccgcugcg   420 gcacugaaga gaaagcgga agcggcagaa gcagcugcag cugaagcaag aaagaaagcg   480
gcaacugaag cugcugaaaa agccaaagca gaagcugaga gaaagcggc ugcugaaaag   540 gcugcagcug auaaggcaaa auucagcacg cccgucugga uaagccaggc gcaaggcauc   600
cgugcuggcc cucaacgccu caccuaauga auaacuaauc caaucgaauu cccgcggccg   660
c                                                                   661
```

<210> SEQ ID NO 9
<211> LENGTH: 37
<212> TYPE: PRT
<213> ORGANISM: Artificial Sequence
<220> FEATURE:
<221> NAME/KEY: FORMYLATION
<222> LOCATION: 1
<220> FEATURE:
<223> OTHER INFORMATION: Synthetic peptide fragment

<400> SEQUENCE: 9

Met Asp Tyr Lys Asp Asp Asp Lys Gly His His His His His
1               5                   10                  15

Gly Cys Lys Arg Leu Arg Gly Pro Trp Glu Trp Leu Arg Cys Gly Glu
            20                  25                  30

Asn Leu Tyr Phe Gln
        35

<210> SEQ ID NO 10
<211> LENGTH: 638
<212> TYPE: RNA
<213> ORGANISM: Artificial Sequence
<220> FEATURE:
<223> OTHER INFORMATION: Designed RNA to code a peptide having affinity
      for HSP90

<400> SEQUENCE: 10
gggagaccac aacgguuucc cucuagaaau aauuuuguuu aacuuuaaga aggagauaua      60
ccaauggacu auaaagauga cgaugacaaa ggucaccauc aucaccauca cgguugcugg     120
guguuccguu ggggcaagug gucugcgugc ggcgaaaacc uguauuucca gggcggugca     180
gguggcagcg gaggugguug cagcggaggu gaauaucaag gccaaucguc ugaccagaag     240
caagcugaag aggcggcagc gaaagcggcg gcagaugcua aagcgaaggc cgaagcagau     300
gcuaaagcug cggaagaagc agcgaagaaa cggcugcag acgcaaagaa aaaagcagaa     360
gcagaagccg ccaaagccgc agccgaagcg cagaaaaaag ccgaggcagc cgcugcggca     420
cugaagaaga aagcggaagc ggcagaagca gcugcagcug aagcaagaaa gaaagcggca     480
acugaagcug cugaaaaagc caaagcagaa gcugagaaga agcggcugc ugaaaaggcu     540 gcagcugaua aggcaaaauu cagcacgccc gucuggauaa gccaggcgca aggcauccgu     600
gcuggcccuc aacgccucac cuaaugaaua acuaaaucc                          638

<210> SEQ ID NO 11
<211> LENGTH: 652
<212> TYPE: RNA
<213> ORGANISM: Artificial Sequence
<220> FEATURE:
<223> OTHER INFORMATION: Designed RNA to code a peptide having affinity
      for HSP90

<400> SEQUENCE: 11
gggagaccac aacgguuucc cucuagaaau aauuuuguuu aacuuuaaga aggagauaua      60
ccaauggacu auaaagauga cgaugauaag ggcugugcgg ggcguuggaa uguucugugg     120
aggacguaua cuuauaugca cuguggugag aaucucuacu uucaagguggg cgccggugc     180 agcggaggug guggcagcgg aggugaauau caaggccaau cgucugacca gaagcaagcu     240
gaagaggcgg cagcgaaagc ggcggcagau gcuaaagcga aggccgaagc agaugcuaaa     300
gcugcggaag aagcagcgaa gaaagcggcu gcagacgcaa agaaaaaagc agaagcagaa     360

```
gccgccaaag ccgcagccga agcgcagaaa aaagccgagg cagccgcugc ggcacugaag    420
aagaaagcgg aagcggcaga agcagcugca gcugaagcaa gaaagaaagc ggcaacugaa    480
gcugcugaaa aagccaaagc agaagcugag aagaaagcgg cugcugaaaa ggcugcagcu    540
gauaaggcaa aauucagcac gcccgucugg auaagccagg cgcaaggcau ccgugcuggc    600
ccucaacgcc ucaccuaaug aauaacuaau ccagucacgu aucgagucau gc            652
```

<210> SEQ ID NO 12
<211> LENGTH: 34
<212> TYPE: PRT
<213> ORGANISM: Artificial Sequence
<220> FEATURE:
<223> OTHER INFORMATION: Designed peptide having affinity for HSP90

<400> SEQUENCE: 12

```
Met Asp Tyr Lys Asp Asp Asp Lys Gly Cys Val Arg Leu Trp Val
1               5                   10                  15

Arg Phe Arg Gly Leu Arg Trp Arg Leu Tyr Cys Gly Glu Asn Leu Tyr
                20                  25                  30

Phe Gln
```

<210> SEQ ID NO 13
<211> LENGTH: 30
<212> TYPE: PRT
<213> ORGANISM: Artificial Sequence
<220> FEATURE:
<223> OTHER INFORMATION: Designed peptide having affinity for HSP90

<400> SEQUENCE: 13

```
Met Asp Tyr Lys Asp Asp Asp Lys Gly Cys Leu Ser Arg Leu Ala
1               5                   10                  15

Tyr Arg Pro Trp Tyr Leu Cys Gly Glu Asn Leu Tyr Phe Gln
                20                  25                  30
```

<210> SEQ ID NO 14
<211> LENGTH: 30
<212> TYPE: PRT
<213> ORGANISM: Artificial Sequence
<220> FEATURE:
<223> OTHER INFORMATION: Designed peptide having affinity for HSP90

<400> SEQUENCE: 14

```
Met Asp Tyr Lys Asp Asp Asp Lys Gly Cys Leu Ile Leu Pro Tyr
1               5                   10                  15

Ser His Thr Gly Trp Gln Cys Gly Glu Asn Leu Tyr Phe Gln
                20                  25                  30
```

RIBOSOME DISPLAY COMPLEX AND PRODUCTION METHOD THEREFOR

TECHNICAL FIELD

One or more embodiments of the present invention relate to a novel ribosome display complex and a production method therefor.

BACKGROUND

In recent years, a therapeutic agent for a specific disease and a molecule having a high affinity for a target molecule have been searched from a polypeptide library having various amino acid sequences. It is thought that the reason for this is that a polypeptide has fewer side effects than a low molecular weight compound due to high specificity and selectivity of a polypeptide. In addition, a polypeptide has an advantage that a library containing many polypeptides can be prepared more easily than a library of a low molecular weight compound, since DNA encoding a polypeptide in which the amino acid sequence in a specific part is randomized can be readily obtained by a PCR technique using a random primer (Non-patent documents 1 to 3).

It has attracted attention to develop a pharmaceutical product of which function is expanded by chemically modifying a polypeptide such as an antibody with a functional molecule. For example, it is described in Non-patent documents 4 and 5 that an antibody-drug conjugate (ADC) was applied as an anticancer drug. Such a compound formed by binding a polypeptide and a functional molecule has been a focus of attention in the drug discovery field, since a property of a polypeptide and a function of a functional molecule are combined, and each characteristic is exploited and each shortcoming is compensated (Non-patent documents 6 to 10).

For example, since a polypeptide has high specificity for a target molecule, a polypeptide is considered to have lower side effect than a low molecular weight drug. On the one hand, a polypeptide is not stable, since a polypeptide is degraded by an enzyme such as protease and peptidase in a living body. Accordingly, the stability of a peptide in a living body may be improved by introducing an unnatural amino acid or cyclizing the peptide with a modifying reagent. In addition, since the structure of a polypeptide becomes stable by cyclization, an affinity for and a selectivity to a target compound may be improved, and a resistance to a degrading enzyme and a cell membrane permeability may be obtained (Non-patent documents 6 to 10).

Thus, a technology to prepare a library containing polypeptides to which a functional molecule such as a modifying reagent for cyclization and an anticancer drug is bound is brought to attention.

As such a technology to prepare a library containing compounds formed by binding a functional molecule and a polypeptide, a complex in which a displayed polypeptide (phenotype) corresponds to the gene encoding the polypeptide (genotype) on a one-to-one basis has been known (Non-patent document 1).

As the above-described method, phage display method is often used. In phage display method, a method for preparing a library by displaying a polypeptide on a bacteriophage and modifying the polypeptide has been known. A library can be produced by such phage display method at low cost by using comparatively simple equipment. The prepared library can be used for screening to isolate a useful polypeptide. There is, however, only a few report of the examples thereof, since the procedure to specifically bind a polypeptide displayed on a phage and a functional molecule is difficult and the process is cumbersome due to many steps (Non-patent documents 6, 7 and 10).

As a library of polypeptides to which a functional molecule is bound, a library obtained by inserting a special amino acid into a specific position of a polypeptide chain in translation system in vitro and reacting the amino acid residue in the peptide with a reactive functional group to cyclize the peptide (Non-patent documents 8 and 9). In addition, a method for cyclizing a peptide by directly reacting an mRNA-peptide complex with a modifying reagent in mRNA display method is reported (Non-patent document 9).

The above-described method for preparing a library using in vitro translation system is very superior to phage display method in terms of variation. As the in vitro translation system method, ribosome display method (RD method), mRNA display method and cDNA display method are exemplified. Among the exemplified methods, ribosome display method (RD method) is excellent, since a library containing $10^{12}$ or more kinds of polypeptides can be produced in several minutes by merely mixing in vitro translation system and mRNA. On the one hand, mRNA display method and cDNA display method are cumbersome, since the number of steps to produce a library is large, such as a step of annealing mRNA and puromycin DNA.

It has not been reported that a functional molecule is bound to a polypeptide in RD method. The reason for this is that a phenotype-genotype complex used in RD method is formed by non-covalently biding a displayed peptide and a nucleic acid containing a gene through a ribosome and a ribosome itself is vulnerable to a reaction to bind a functional molecule. Specifically, the reason why it has been not reported that a functional molecule is bound in RD method is that 1) a complex in RD method is more unstable than that of mRNA display method, since a phenotype-genotype complex is produced by a covalent bond in mRNA display method, and 2) the functions of a ribosome and a complex tend to become poor by binding a functional molecule, since cysteine and lysine contained in a ribosomal protein which constitutes a ribosome are reactive. In fact, for example, there are totally 36 cysteines and 686 lysines in 55 kinds of ribosomal proteins of *Escherichia coli*.

For example, cysteine plays a structurally and functionally important role as a residue of a polypeptide. A SH group of a cysteine residue forms a disulfide bona with a SH group of a cysteine residue of the same polypeptide and other polypeptide. The disulfide bond often contributes to a higher order structure of a polypeptide. Since a SH group not only forms a disulfide bond but also acts as a substrate of various reactions, a SH group is a good candidate as a modification site in the case where a polypeptide chain is artificially modified. On the one hand, when a specific cysteine residue is specifically modified, another cysteine residue at other unintentional position may be often reacted due to the high reactivity thereof. As a result, a higher order structure of a polypeptide is often broken. The same applies to lysine, histidine and tryptophan. Thus, it is not easy to devise a method for modifying a target cysteine without impairing the function thereof in a polypeptide, a ribosome and a RD complex containing a polypeptide and a ribosome having a plurality of cysteine, lysine, histidine and tryptophan. Specifically, a complicated reaction step procedure is required, such as a method for removing an unintended cysteine from a ribosomal protein by a genetic engineering and a preliminary reaction by which an unintended cysteine becomes unreactive. If such a step is included in a method for producing a library, an advantage that a library can be produced with fewer steps as a characteristics of RD method is lost.

NON-PATENT DOCUMENT

Non-patent document 1: H. Leemhuis, other 3 persons, "New genotype-phenotype linkages for directed evolution of functional proteins", Current Opinion in Structural Biology 2005, 15: 472-478

Non-patent document 2: D. Lipovsek, other 1 person, "In-vitro protein evolution by ribosome display and mRNA display", Journal of immunological methods, 290(2004), 51-67

Non-patent document 3: H. M. E. Azzazy, other 1 person, "Phage display technology: clinical applications and recent innovations", Clinical Biochemistry, 35(2002), 425-445

Non-patent document 4: H. L. Perez, other 6 persons, "Antibody-drug conjugates: current status and future directions", Drug Discovery Today, Volume 19, Number 7, July 2014

Non-patent document 5: S. C. Alley, other 2 persons, "Antibody-drug conjugates: targeted drug delivery for cancer", Current Opinion in Chemical Biology, 2010, 14: 529-537

Non-patent document 6: C. Heinis, other 3 persons, "Phage-encoded combinatorial chemical libraries based on bicyclic peptides", Nature Chemical Biology, 5, 502-507 (2009)

Non-patent document 7: I. R. Rebollo, other 1 person, "Phage selection of bicyclic peptides", Methods 60(2013), 46-54

Non-patent document 8: T. Kawakami, other 2 persons, "Messenger RNA-Programmed Incorporation of Multiple N-Methyl-Amino Acids into Linear and Cyclic Peptides", Chemistry & Biology, vol. 15(1), p. 32-42, January 2008

Non-patent document 9: K. Josephson, other 2 persons, "mRNA display: from basic principles to macrocycle drug discovery", Drug Discovery Today, volume 19, Number 4, April 2014, pp. 388-399

Non-patent document 10: K. Fukunaga, other 4 persons, "Construction of a crown ether-like supramolecular library by conjugation of genetically-encoded peptide linkers displayed on bacteriophage T7", Chemical Communications, 2014, 50, 3921-3923

In fact, the present inventors experimentally confirmed that when the inventors tried to produce a RD complex after a ribosome is reacted with a cyclizing reagent, DBP: 1,3-dibromo-2-propanone, as a modifying reagent, a RD complex cannot be formed.

SUMMARY

Accordingly, one or more embodiments of the present invention provide a ribosome complex which can be produced without a complicated reaction procedure and of which displayed polypeptide is modified without impairing a function of the ribosome, particularly function to produce a polypeptide library, and a method for producing the ribosome complex.

The inventors intensively studied and found that when a library of modified polypeptides is prepared by ribosome display method and a polypeptide is modified by an artificial material, there is a risk of losing the function of the polypeptide, since an amino acid reside has a reactive side chain functional group, such as cysteine, in a ribosomal protein of a ribosome; but an adhesive function of a ribosome to bind RNA to the polypeptide translated from the RNA can be maintained without losing the inherent function and a polypeptide in a ribosome display complex can be easily modified by modifying a polypeptide with an artificial material at an appropriate timing.

Hereinafter, one or more embodiments of the present invention are described.

[1] A method for producing a ribosome display complex, wherein the ribosome display complex comprises a polypeptide chain, an mRNA molecule and a ribosome, the polypeptide chain comprises 1 or more reactive amino acid residues selected from the group consisting of a cysteine residue, a lysine residue, a histidine residue and a tryptophan residue, a side chain reactive functional group of the reactive amino acid residue is modified, and the mRNA molecule comprises a base sequence encoding an amino acid sequence of the polypeptide chain, comprising the steps of:

translating the mRNA molecule in a cell-free peptide synthesis system utilizing the ribosome to obtain a ribosome complex comprising an unmodified polypeptide chain, the mRNA molecule and the ribosome, and modifying the unmodified polypeptide chain by reacting the side chain reactive functional group in the unmodified polypeptide chain with a modifying reagent.

[2] The method for producing the ribosome display complex according to the above [1], wherein the modifying reagent is a compound represented by the following formula (1):

(1)

wherein A is a group capable of forming a linkage by reacting with a side chain of the cysteine residue, the lysine residue, the histidine residue or the tryptophan residue, B is a linker group or a single bond, C is a functional group, a is an integer of 1 or more, c is 0 or an integer of 1 or more, provided that when the a is an integer of 2 or more, a plurality of A are the same as or different from each other.

[3] The method for producing the ribosome display complex according to the above [2], wherein the A is a halogenated alkyl group, an activated carbonyl group, an unsaturated hydrocarbon group, an epoxy group, a sulfonyl-containing group, an isocyanate group, an isothiocyanate group, a carbene-precursor group, a carbene-containing group, a disulfide bond-containing group or a thiol group.

[4] The method for producing the ribosome display complex according to the above [2] or [3], wherein the linker group B is a group having one or more selected from a hetero atom-containing polar group, a chained or cyclic aliphatic hydrocarbon group optionally having a hetero atom-containing polar group between carbon atoms and optionally having a substituent group, and an aromatic ring optionally having a substituent group solely or in combination, the hetero atom-containing polar group is —O—, —S—, —NR$^1$— (wherein R$^1$ is a hydrogen atom, a hydrocarbon group or an atomic bonding at a terminal of the linker group), —CO—, —COO—, —CONR$^2$— (wherein R$^2$ is a hydrogen atom, a hydrocarbon group or an atomic bonding at a terminal of the linker group), —N=N— or —SO$_2$—, the substituent group on the aliphatic hydrocarbon group is a halogeno group, an aryl group, a carboxy group, an alkoxycarbonyl group or a hydroxy group, the substituent group on the aromatic ring is a halogeno group, an alkyl group, an aralkyl group, a carboxy group, an alkoxycarbonyl group, a hydroxyalkyl group or a carboxyalkyl group.

[5] The method for producing the ribosome display complex according to the above [4], wherein the linker group B has -B1- unit, -B2- unit, -B2-B1- unit or - B2-B1-B3- unit, the B1 is a group having one or more selected from a chained or cyclic aliphatic hydrocarbon group optionally having a hetero atom-containing polar group between carbon atoms and optionally having a substituent group, and an aromatic ring optionally having a substituent group solely or in combination, B2 and B3 are independently hetero atom-containing polar groups, B1 or B2 are bound to the A, the hetero atom-containing polar group and the substituent group have the same meanings as the above.

[6] The method for producing the ribosome display complex according to the above [5], wherein the modifying reagent is any one of compounds represented by the following formulae:

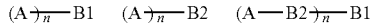

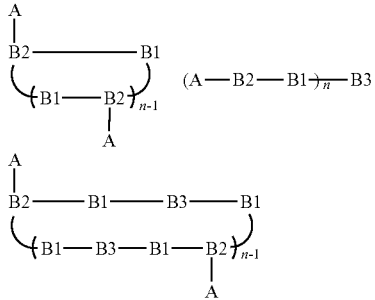

wherein A, B1, B2 and B3 have the same meanings as the above, n is an integer of 1 or more, one or more of B1, B2 and B3 may be bound by the one or more C.

[7] The method for producing the ribosome display complex according to any one of the above [2] to [6], when the A is the halogenated alkyl group, a carbon atom, bound by the halogeno group in the halogenated alkyl group is a carbon atom at a position of the carbonyl group or a carbon atom directly binding to the aromatic ring.

[8] The method for producing the ribosome display complex according to any one of the above [2] to [7], wherein the polypeptide chain comprises 2 or more reactive amino acid residues selected from the group consisting of the cysteine residue, the lysine residue, the histidine residue and the tryptophan residue, the a is 2 or more in the modifying reagent represented by the formula (1), a ring is formed by the polypeptide chain and the modifying reagent in the step of reacting the side chain reactive functional group in the unmodified polypeptide chain with the modifying reagent.

[9] The method for producing the ribosome display complex according to any one of the above [1] to [8], wherein the polypeptide chain has 100 to 5000 amino acid residues.

[10] The method for producing the ribosome display complex according to any one of the above [1] to [9], wherein the reactive amino acid residue is included between a $2^{nd}$ position from an N-terminal and a $30^{th}$ position from a C-terminal inclusive in the polypeptide chain.

[11] The method for producing the ribosome display complex according to any one of the above [1] to [10], wherein a random, sequence having 1 to 30 amino acid residues is included between a $2^{nd}$ position from, an N-terminal and a $30^{th}$ position from a C-terminal inclusive in the polypeptide chain.

[12] The method for producing the ribosome display complex according to any one of the above [1] to [11], wherein the ribosome is source a from *Escherichia coli*.

[13] A ribosome display complex, comprising a polypeptide chain, an mRNA molecule and a ribosome, wherein the polypeptide chain comprises 1 or more reactive amino acid residues selected from the group consisting of a cysteine residue, a lysine residue, a histidine residue and a tryptophan residue, a side chain reactive functional group of the 1 or more reactive amino acid residues is modified, and the mRNA molecule comprises a base sequence encoding an amino acid sequence of the polypeptide chain.

[14] The ribosome display complex according to the above [13], wherein a modification structure of the side chain reactive functional group is a chemical structure represented by the following formula (2):

wherein Ax is a binding group formed by reacting with a side chain of the cysteine residue, the lysine residue, the histidine residue or the tryptophan residue, B is a linker group or a single bond, C is a functional group, a is an integer of 1 or more, c is 0 or an integer of 1 or more, provided that when the a is an integer of 2 or more, a plurality of Ax are the same as or different from each other.

[15] The ribosome display complex according to the above [14], wherein the Ax is a chemical bond formed by reacting a halogenated alkyl group, an activated carbonyl group, an unsaturated hydrocarbon group, an epoxy group, a sulfonyl-containing group, an isocyanate group, an isothiocyanate group, a carbene-precursor group, a carbene-containing group, a disulfide bond-containing group or a thiol group with the side chain of the cysteine residue, the lysine residue, the histidine residue or the tryptophan residue.

[16] The ribosome display complex according to the above [15], wherein the linker group B is a group having one or more selected from a hetero atom-containing polar group, a chained or cyclic aliphatic hydrocarbon group optionally having a hetero atom-containing polar group between carbon atoms and optionally having a substituent group, and an aromatic ring optionally having a substituent group solely or in combination, the hetero atom-containing polar group is —O—, —S—, —NR$^1$— (wherein R$^1$ is a hydrogen atom, a hydrocarbon group or an atomic bonding at a terminal of the linker group), —CO—, —COO—, —CONR$^2$— (wherein R$^2$ is a hydrogen atom, a hydrocarbon group or an atomic bonding at a terminal of the linker group), —N=N— or —SO$_2$—, the substituent group on the aliphatic hydrocarbon group is a halogeno group, an aryl group, a carboxy group, an alkoxycarbonyl group or a hydroxy group, the substituent group on the aromatic ring is a halogeno group, an alkyl group, an aralkyl group, a carboxy group, an alkoxycarbonyl group, a hydroxyalkyl group or a carboxyalkyl group.

[17] The ribosome display complex according to the above [16], wherein the linker group B has -B1- unit, -B2- unit, -B2-B1- unit or -B2-B1-B3- unit, the B1 is a group having one or more selected from a chained or cyclic aliphatic hydrocarbon group optionally having a hetero atom-containing polar group between carbon atoms and optionally having a substituent group, and an aromatic ring optionally having a substituent group solely or in combination, B2 and B3 are independently hetero atom-containing polar groups, B1 or B2 is bound to the Ax, the hetero atom-containing polar group and the substituent group have the same meanings as the above.

[18] The ribosome display complex according to the above [17], wherein the modification structure is represented by the following formulae:

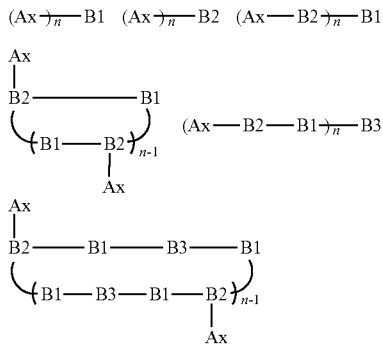

wherein Ax, B1, B2 and B3 have the same meanings as the above, n is an integer of 1 or more, one or more of B1, B2 and B3 may be bound by the one or more C.

[19] The ribosome display complex according to any one of the above [14] to [18], when the Ax is a chemical bond formed between a halogenated alkyl group and the side chain of the cysteine residue, the lysine residue, the histidine residue or the tryptophan residue, a carbon atom bound by the halogeno group in the halogenated alkyl group is a carbon atom at α position of the carbonyl group or a carbon atom directly binding to the aromatic ring.

[20] The ribosome display complex according to any one of the above [14] to [19], wherein the polypeptide chain comprises 2 or more reactive amino acid residues selected from the group consisting of the cysteine residue, the lysine residue, the histidine residue and the tryptophan residue, the a is 2 or more in the modification structure represented by the formula (2), a ring is formed by the polypeptide chain and the modification structure.

[21] The ribosome display complex according to any one of the above [13] to [20], wherein the polypeptide chain consists of 100 to 5000 amino acid residues.

[22] The ribosome display complex according to any one of the above [13] to [21], wherein the reactive amino acid residue is included between a $2^{nd}$ position from an N-terminal and a $30^{th}$ position from a C-terminal inclusive in the polypeptide chain,

[23] The ribosome display complex according to any one of the above [13] to [22], wherein a random sequence having 1 to 30 amino acid residues is included between a $2^{nd}$ position from an N-terminal and a $30^{th}$ position from a C-terminal inclusive in the polypeptide chain.

[24] The ribosome display complex according to any one of the above [13] to [23], wherein the ribosome is sourced from *Escherichia coli*.

According to one or more embodiments of the present invention, a ribosome complex of which cysteine residue, lysine residue, histidine residue or tryptophan residue in a displayed polypeptide is modified with a functional molecule can be provided by very simple and easy steps. A ribosomal protein which constitutes a ribosome complex has a much larger number of amino acid reside having a reactive side chain functional group, such as a cysteine residue, than a displayed polypeptide. In consideration of this fact, the above-described effect is very surprising. Specifically, a ribosome is composed of 55 ribosomal proteins and 3 RNA, and a certain ribosome totally contains 36 cysteines, 686 lysines and 151 histidines. Nevertheless, according to one or more embodiments of the present invention, a displayed polypeptide can be chemically modified by the very simple step without inhibiting the adhesive function between the polypeptide and m RNA, in other words, with maintaining a RD complex. Such an effect according to one or more embodiments of the present invention is unpredictable and extremely useful.

DETAILED DESCRIPTION OF THE EMDOBIMENTS

Figure 1:
FIG. 1 is a schematic diagram, of the template DNA used for preparing the ribosome display complex according to one or more embodiments of the present invention.

Hereinafter, first, a method for producing a ribosome display complex according to one or more embodiments of the present invention is described.

(1) Step of Preparing Ribosome Display Complex

In this step, an mRNA molecule is translated by a cell-free peptide synthesis system using a ribosome to obtain a ribosome complex which contains an unmodified polypeptide chain, the mRNA molecule and the ribosome.

A cell-free peptide synthesis system utilizing a ribosome uses a compound which is needed for synthesizing a polypeptide on the basis of RNA information in a cell and synthesizes a polypeptide from mRNA in vitro. Specifically, an mRNA molecule is added into a reaction system, which contains a protein needed for a translation of the mRNA and an energy regeneration, a ribosome, tRNA, an amino acid, NTP, a buffer solution and the like in order to synthesis a polypeptide on the basis of the added mRNA. The protein is exemplified by an initiation factor, an elongation factor and an aminoacyl-tRNA synthetase. Since a kit for a cell-free peptide synthesis is commercially available, reagents contained in such a kit may be used except for an mRNA molecule.

A ribosome display complex prepared in the present step contains an mRNA, a polypeptide chain translated from the mRNA, and a ribosome. Hereinafter, a ribosome display is abbreviated as "RD" in some cases.

The polypeptide chain contained in the RD complex according to one or more embodiments of the present invention contains one or more reactive amino acid residues selected from the group consisting of a cysteine residue, a lysine residue, a histidine residue, and a tryptophan residue. The reactive amino acid residue is used for a modification in the next step. The number of the reactive amino acid residue is preferably 2 or more, since the stability may be further improved in some cases by cyclizing the polypeptide chain. On the one hand, the number of the reactive amino acid residue is preferably 10 or less, since the number and the position of a modifying reagent bound to RD complex may not be controllable due to many reactive points and it may become difficult to compare the properties of the polypeptide chain on the basis of an amino acid sequence.

As the above-described reactive amino acid residue, a cysteine residue and/or a lysine residue is preferred. In addition, for example, when a cysteine residue contributes to a stability of a higher order structure of a polypeptide by a disulfide bond, it is preferred that another reactive amino acid residue is introduced.

The position of the reactive amino acid residue may be appropriately selected, and the position is exemplified by an outside part from an exit tunnel of the ribosome. Specifically, it is preferred that the position is from the $2^{nd}$ position from the N-terminal through the $30^{th}$ position from the C-terminal, provided that the $2^{nd}$ position from the N-terminal and the $30^{th}$ position from the C-terminal are included in the preferable position. Since the polypeptide chain is modified in the RD complex in one or more embodiments of the present invention, it can be difficult to sterically inhibit the modification reaction in the case where the reactive amino acid residue is located at the above-described position. The above-described position of the reactive amino acid residue from the C-terminal side is preferably the $50^{th}$ position and more preferably the $100^{th}$ position. The position of the reactive amino acid residue from the N-terminal side may be appropriately determined depending on the chain length of the polypeptide, and is exemplified by from the $2^{nd}$ position through the $1000^{th}$ position from the N-terminal, preferably from the $2^{nd}$ position through the $100^{th}$ position from the N-terminal, and more preferably from the $2^{nd}$ position through the $50^{th}$ position from the N-terminal.

It is preferred that the polypeptide chain contains a random sequence in a specific position for a useful polypeptide library. From, such a random sequence, a useful amino acid sequence for a predetermined purpose can be specified. The position of the random sequence may be appropriately selected, and for example, it is preferred that the position is from the $2^{nd}$ position from the N-terminal through the $30^{th}$ position from the C-terminal, provided that the $2^{nd}$ position from the N-terminal and the $30^{th}$ position from the C-terminal are included in the preferable position, similarly to the position of the reactive amino acid residue. In other words, it is preferred that the reactive amino acid residue is included in the random sequence. Accordingly, the preferred position of the random sequence can be determined in the same range as the preferred position of the reactive amino acid residue. The number of the amino acid of the random sequence may be appropriately adjusted, and for example, may be 1 or more and 30 or less. The upper limit number of the amino acid of the random sequence is not particularly restricted, and is preferably 10. The number of the random sequence in the polypeptide chain may be 1 and 2 or more. When the one random sequence is longer or the number of the random sequence is larger, the diversity of a polypeptide library can be improved more surely.

The polypeptide chain may have an amino acid sequence for various purposes. Such a sequence is exemplified by a sequence for the purification of a polypeptide chain, such as FLAG$^{(R)}$ sequence and poly His sequence, a sequence which is selectively cleaved by a protease or the like, and a spacer sequence.

The mRNA has at least the base sequence which encodes the above-described polypeptide chain. In addition, the mRNA may contain a sequence necessary for a translation or the like. The mRNA encodes the polypeptide in the same RD complex; therefore, when a specific RD complex is selected in a library, the amino acid sequence of a useful polypeptide can be indirectly specified by analyzing the base sequence of the mRNA.

The number of the amino acid residue of the polypeptide chain is not particularly restricted, and for example, may be 100 or more and 5000 or less. The number of the amino acid residue is more preferably 150 or more, even more preferably 200 or more, and more preferably not more than 800 or not more than 600, even more preferably 500 or less.

As the ribosome, a ribosome which is purified from a living body can be used. For example, a ribosome sourced from *Escherichia coli* bacterium may be used.

In a polypeptide synthesis in a cell, after a polypeptide is synthesized, a dissociation factor binds to a stop codon of mRNA, a polypeptide is released and mRNA dissociates from a ribosome. On the one hand, since one or more embodiments of the present step produce a RD complex containing a polypeptide chain, mRNA and a ribosome, the polypeptide chain must not be released. Thus, a publically-known procedure not to release the polypeptide may be applied. For example, as such a procedure, a stop codon is removed from mRNA, a translation elongation arrest sequence called as an arrest sequence is located at the 3' end of mRNA, and a dissociation factor and a ribosome regenerating factor are not used in the cell-free peptide synthesis system.

After a RD complex is synthesized, an ordinary method for purifying a RD complex may be applied. For example, when the polypeptide chain contains FLAG$^{(R)}$ sequence or a poly His sequence, a publically-known purification method suitable for the sequence may be applied.

(2) Step of Modifying Polypeptide Chain

After the ribosome complex containing the unmodified polypeptide chain, mRNA molecule and ribosome is produced as the above, in this step, the unmodified polypeptide chain is modified by reacting the side chain reactive functional group in the unmodified polypeptide chain with a modifying reagent. In the case where the ribosome complex containing the unmodified polypeptide chain is produced and then the ribosome complex is reacted with a modifying reagent, the polypeptide chain can be chemically modified by a very simple step with maintaining the RD complex, in other words, without inhibiting the ribosome's function to adhere the polypeptide and mRNA.

Since a ribosome is a large molecule as a complex of rRNA and proteins, a ribosome contains more reactive amino acid residues than the displayed polypeptide contained in a RD complex. Nevertheless, even if a RD complex is produced and the RD complex is subsequently reacted with a modifying reagent, the displayed polypeptide chain in the RD complex can be modified and the RD complex can be maintained.

As a modifying reagent used for modifying the unmodified polypeptide chain, for example, the compound represented by the following formula (1) can be used.

(1)

In the above formula, 'A' is a group capable of forming a linkage by reacting with a side chain of the cysteine residue, the lysine residue, the histidine residue or the tryptophan residue, specifically, a group capable of forming a linkage by reacting with a thiol group of the cysteine residue, a side chain amino group (—NH$_2$) of the lysine residue, or a side chain amino group (>NH) of the histidine residue and the tryptophan residue.

Specifically, 'A' is exemplified by a halogenated alkyl group, an activated carbonyl group, an unsaturated hydrocarbon group, an epoxy group, a sulfonyl-containing group, an isocyanate group, an isothiocyanate group, a carbene-precursor group, a carbene-containing group, a disulfide bond-containing group and a thiol group.

The halogeno group in the halogenated alkyl group is exemplified by a chloro group, a bromo group and an iodo group. The alkylene group in the halogenated alkyl group may be a linear alkylene group or a branched alkylene group, and is exemplified by a $C_{1-20}$ alkylene group, preferably a $C_{1-10}$ alkylene group, more preferably a $C_{1-6}$ alkylene group or a $C_{1-4}$ alkylene group, and even more preferably a $C_{1-2}$ alkylene group. It is preferred that the carbon atom bound to the halogeno group in the halogenated alkyl group directly binds to the carbonyl group or aromatic ring in 'B'. The halogenated alkyl group can bind to a thiol group and an amino group.

The activated carbonyl group contains an activated ester group, a formyl group or the like. The activated ester group is exemplified by an imide ester group such as a succinimide group, 4-nitrophenol ester group, HOBt ester group, HOAt ester group and Oxyma ester group. The activated carbonyl group can bind to, for example, a side chain thiol group of a cysteine residue and an amino group. The formyl group can bind to, for example, a side chain amino group of lysine by reductive amination reaction.

The unsaturated hydrocarbon group means an unsaturated hydrocarbon group having at least one of a carbon-carbon double bond or a carbon-carbon triple bond, contains a vinyl group, a propargyl group or the like, and is preferably exemplified by a vinylcarbonyl group, a propargylcarbonyl group and a vinylsulfonyl group. The unsaturated hydrocarbon group can be bound to, for example, an amino acid and a thiol group by Michael addition or nucleophilic substitution reaction.

The sulfonyl-containing group is exemplified by an alkylsulfonyl group, an arylsulfonyl group, a sulfonate ester group such as an alkylsulfonyloxy group and an arylsulfonyloxy group, and can be reacted with a thiol group and an amino group as a leaving group. The alkylsulfonyl group is exemplified by a methanesulfonyl group, a chloromethanesulfonyl group and a trifluoromethanesulfonyl group. The arylsulfonyl group is exemplified by a benzenesulfonyl group and a toluenesulfonyl group. The sulfonate ester group is exemplified by a methanesulfonyloxy group, a chloromethanesulfonyloxy group, a trifluoromethanesulfonyloxy group, a benzenesulfonyloxy group and a toluenesulfonyloxy group.

The carbene-precursor group is exemplified by a diazo-containing group and a diazirine structure-containing group, and preferably a group in which a diazo group is bound to a carbon atom adjacent to a carbonyl group. A diazo group is eliminated from, the carbene-precursor group; as a result, a carbene is generated to be bound to thiol. In addition, as the carbene-containing group, groups obtained by generating a carbene from various carbene-precursor groups are exemplified.

The disulfide bond-containing group and a thiol group can form a disulfide bond with a side chain thiol group of the cysteine residue.

The epoxy group, isocyanate group and isothiocyanate group can react with both of a thiol group and an amino group.

The number of 'A', i.e. 'a', is preferably an integer of 2 or more. When 'A' is 2 or more and there are the 2 or more side chain reactive functional groups, the polypeptide chain can be cyclized. The stability of the cyclized polypeptide chain may be further improved.

In the above formula, 'B' is a linker group or a single bond. The 'B' as a linker group is exemplified by a hetero atom-containing polar group, an aliphatic hydrocarbon group and an aromatic ring.

The hetero atom-containing polar group is exemplified by —O—, —S—, —NR$^1$— [wherein R$^1$ is a hydrogen atom, a hydrocarbon group (preferably a C$_{1-6}$ alkyl group) or a single bond at the end of the linker group, provided that when R is a single bond, the valence of the linker group is 3 (The same applies hereafter).], —CO—, —COO—, —CONR$^2$— [wherein R$^2$ is a hydrogen atom, a hydrocarbon group (preferably a C$_{1-6}$ alkyl group) or a single bond at the end of the linker group.], —C(=N—R$^3$)— (wherein R$^3$ is a group containing one or more selected from the group consisting of a linear or cyclic aliphatic hydrocarbon group optionally having a substituent, an aromatic ring group or a hetero atom-containing group optionally having a substituent, and a functional group to add some kind of a function, a hydrogen atom, or a single bond at the end of the linker group.), —N=N— and —SO$_2$—.

The aliphatic hydrocarbon group may be any one of a linear alkylene group, a branched alkylene group and a cyclic alkylene group, and is exemplified by a C$_{1-20}$ alkylene group, preferably a C$_{1-10}$ alkylene group, more preferably a C$_{1-6}$ alkylene group or a C$_{1-4}$ alkylene group, and even more preferably a C$_{2-4}$ alkylene group. Between carbon atoms or at the terminal of the aliphatic hydrocarbon group, the above-described hetero atom-containing polar group may be inserted and there may be a substituent. The substituent is exemplified by a halogeno group, an aryl group, a carboxy group, an alkoxycarbonyl group and a hydroxy group. The aryl group is preferably a C$_{6-10}$ aryl group, more preferably a phenyl group or a naphthyl group, and preferably a phenyl group. The number of the substituent is not particularly restricted as long as the substitution is possible, and for example, may be 1 or more and 4 or less, preferably not more than 3 or not more than 2, and preferably 1. When the number of the substituent is 2 or more, the substituents may be the same as or different from each other.

As the aromatic ring group, a C$_{6-10}$ aryl group such as a phenyl group, an indenyl group, a naphthyl group and a biphenyl group is preferred, a phenyl group or a naphthyl group is more preferred, and a phenyl group is preferred. The aromatic ring group may have a substituent. Such a substituent is exemplified by a halogeno group and an alkyl group, preferably a C$_{1-6}$ alkyl group and an aralkyl group, preferably a benzyl group, a carboxy group and an alkoxy-carbonyl group, preferably a (C$_{1-6}$ alkoxy) carbonyl group and a hydroxyalkyl group, preferably a hydroxy-C$_{1-6}$ alkyl group and a carboxyalkyl group, and preferably a carboxy-C$_{1-6}$ alkyl group. The number of the substituent is not particularly restricted as long as the substitution is possible, and for example, may be 1 or more and 4 or less, preferably not more than 3 or not more than 2, and preferably 1. When the number of the substituent is 2 or more, the substituents may be the same as or different from, each other.

The above-described linker 'B' preferably has -B1-, -B2- unit, -B2-B1- unit or -B2-B1-B3- unit. The 'B1' is a single group or a combination group of one or more selected from a linear or cyclic aliphatic hydrocarbon group optionally having a hetero atom-containing polar group between carbon atoms and optionally having a substituent and an aromatic ring optionally having a substituent. The 'B2' and 'B3' are independently a hetero atom-containing polar group. The 'B1' or 'B2' binds to the above-described 'A'. The hetero atom-containing polar group and substituent have the same meanings as the above.

The hetero atom-containing group is exemplified by —O—, —S—, —NR$^3$— [wherein R$^3$ is a hydrogen atom, a hydrocarbon group (preferably a C$_{1-6}$ alkyl group) or a single bond at the end of the linker group, provided that when R is a single bond, the valence of the linker group is 3 (The same applies hereafter.], —CO—, —COO—, —CONR$^4$— [wherein R$^4$ is a hydrogen atom, a hydrocarbon group (preferably a C$_{1-6}$ alkyl group) or a single bond at the end of the linker group.], —N=N— and —SO$_2$—.

In the above formula, 'C' is a functional group to add some kind of function to the polypeptide. Such a functional group may be appropriately selected depending on the purpose and is not particularly restricted. The functional group is exemplified by a linker compound to cyclize the polypeptide, a luminescent substance such as a fluorescent substance, a dye, a radioactive substance, a drug, a toxin, a nucleic acid, an amino acid, a peptide, a sugar, a lipid, a polymer, and a combination thereof. A fluorescent substance is exemplified by a fluorescent dye of a fluorescein, a rhodamine, a coumalin, a pyrene and a cyanine.

The modifying reagent is specifically exemplified by the modifying reagent represented by the following formulae.

 (1a)

 (1b)

 (1c)

 (1d)

 (1e)

(1f)

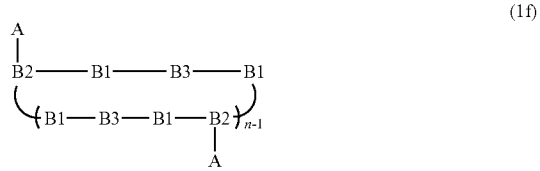

In the above formulae, 'A', 'B1', 'B2' and 'B3' have the same meanings as the above, 'n' is an integer of 1 or more, one or more of 'B1', 'B2' and 'B3' may be bound by the one or more 'C'.

The compounds represented by the above formulae (1a) to (1f) have a functional group 'C', and the functional group 'C' is a group having each of a fluorescent dye or a labeling unit and binds to any one of 'B1', 'B2' and 'B3'. In addition, the functional group 'C' may have a water-soluble substituent such as sulfonic acid group (—SO$_2$—OH) and a sulfonate salt group (—SO$_2$—O$^-$M$^+$) for improving water solubility. The 'M$^+$' is exemplified by an alkali metal ion such as a sodium ion and a potassium ion.

The formula (1a) is specifically exemplified by a compound wherein 'A' is a halogenated alkyl group, an activated carbonyl group (particularly an activated ester group) or an epoxy group, 'B1' is an aliphatic hydrocarbon group or an aromatic ring, 'n' is 2 or 3, and particularly the compound represented by the following formulae.

(1a)

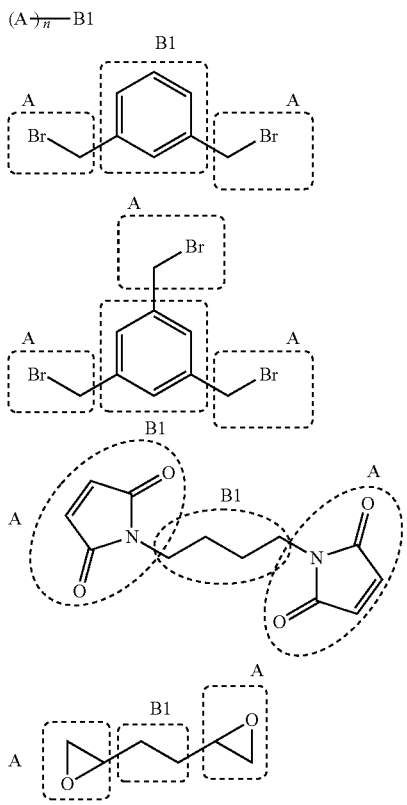

The formula (1b) is specifically exemplified by a compound wherein 'A' is a halogenated alkyl group, 'B2' is an oxygen atom-containing polar group (particularly —CO—), or a nitrogen atom-containing polar group [particularly —C(=N—R⁵)— (wherein $R^5$ is a group containing at least one selected from a linear or cyclic aliphatic hydrocarbon optionally having a substituent, an aromatic ring group and a hetero atom-containing group optionally having a substituent, and a functional group to add some kind of function, a hydrogen atom, or a single bond at the end of the linker group), 'n' is 2, and particularly the compound represented by the following formulae.

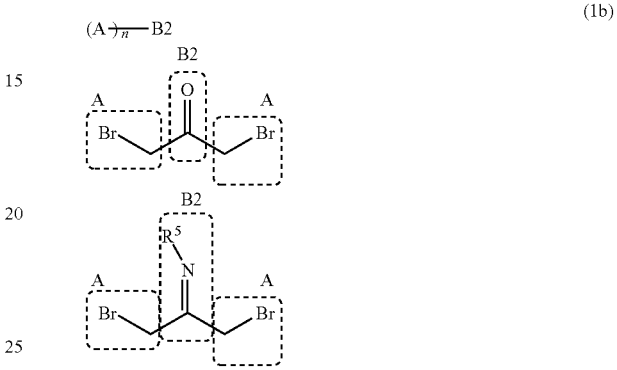

(1b)

The formula (1c) is specifically exemplified by a compound wherein 'A' is a halogenated alkyl group or an activated carbonyl group (particularly an activated ester group), 'B1' is an aliphatic hydrocarbon group, an aliphatic hydrocarbon group having an oxygen atom between carbon atoms, or an aromatic ring, 'B2' is a polar group containing an oxygen atom, a nitrogen atom, or the like (particularly —COO— or —CONH—), 'n' is 1, 2 or 3, and particularly the compound represented by the following formulae.

(1c)

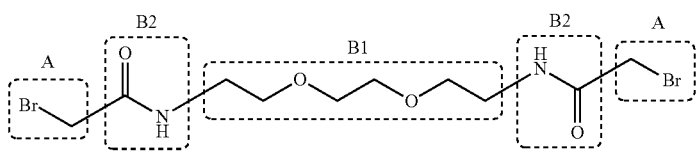

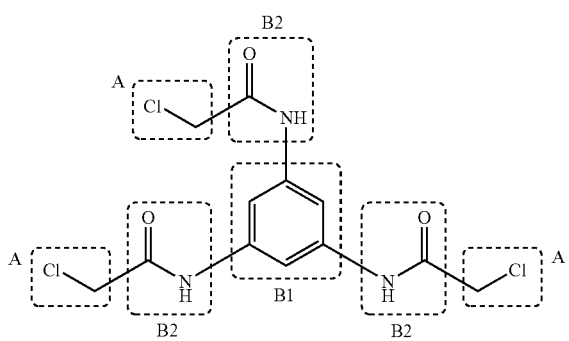

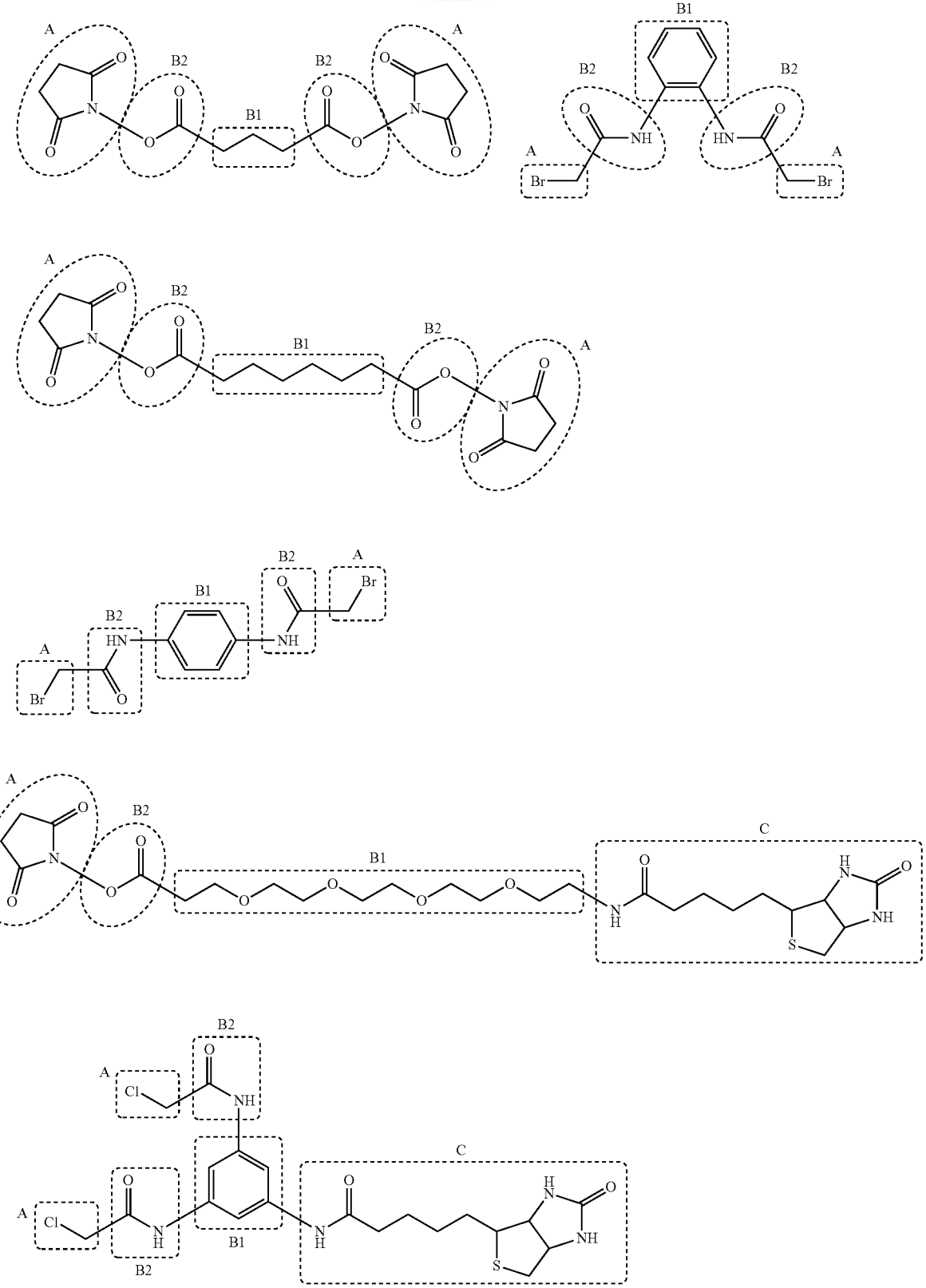
The formula (1d) is specifically exemplified by a compound wherein 'A' is a halogenated alkyl group, 'B1' is an aliphatic hydrocarbon group, 'B2' is a polar group containing an oxygen atom and a nitrogen atom (particularly —CONH—), 'n' is 3, and particularly the compound represented by the following formula.

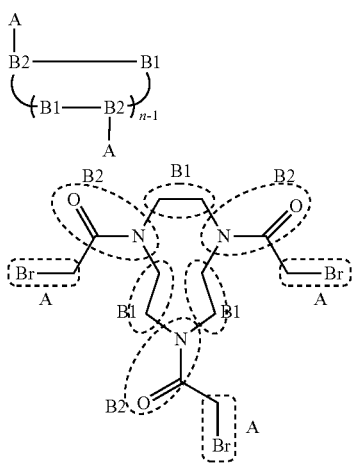

(1d)

The formula (1e) is specifically exemplified by a compound wherein 'A' is a halogenated alkyl group, 'B1' is an aromatic ring, 'B2' and 'B3' are polar groups containing an oxygen atom, a nitrogen atom or the like (particularly —COO— or —N=N), 'n' is 2, and particularly the compound represented by the following formula,

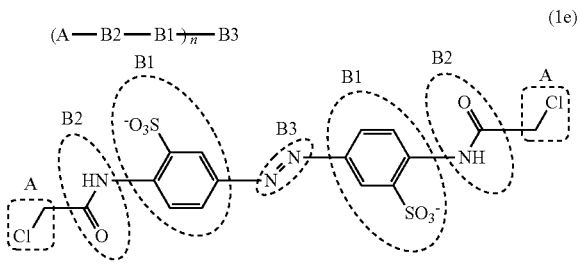

(1e)

The condition to modify the polypeptide chain in the RD complex can be appropriately determined depending on the kind of the side chain reactive functional group to be modified and the modifying reagent to be used. For example, when the side chain thiol group of the cysteine residue should be modified, a disulfide bond is cleaved by a reducing agent to be thiol groups and then a modifying reagent is reacted. As a reducing agent is exemplified by tris(2-carboxyethyl)phosphine sodium salt, dithiothreitol and β-mercaptoethanol.

When a halogenated alkyl group or an epoxy group of the modifying reagent is reacted with a side chain amino group, a base may be added. A base is exemplified by a hydrogen carbonate salt such as sodium hydrogen carbonate; a carbonate salt such as sodium carbonate; a metal hydroxide such as sodium hydroxide; an organic base such as pyridine and triethylamine.

As a reaction solvent for the reaction of the modifying reagent, water is generally used. A reaction temperature may be adjusted to, for example, about 0 to 30° C., preferably about 1 to 20° C., and more preferably 1 to 10° C.

The pH at the time of the reaction of the modifying reagent may be appropriately adjusted depending of the modifying reagent to be used and is not particularly restricted, and may be adjusted to the range of about 4.0 to 10.0, preferably about 5.0 to 9.0, and more preferably about 6.0 to 8.0. The more preferred pH range is different depending on the modifying reagent, and the pH may be adjusted to 7.0 to 7.5 from the viewpoint of suppressing that the number of the introduced modifying reagent per the polypeptide chain becomes 2 or more.

An amount of the modifying reagent can be appropriately determined depending on the kind of the reagent, and the amount to 1 mole of the ribosome complex containing an unmodified polypeptide chain may be adjusted to 1,000 mole or more, preferably 10,000 mole or more, more preferably 60,000 mole or more, and even more preferably 100,000 mole or more. The upper limit thereof is not particularly restricted, and the ratio may be, for example, 100,000,000 mode or less, preferably 50,000,000 mole or less, more preferably 20,000,000 mole or less, and even more preferably 10,000,000 mole or less.

After the polypeptide chain is modified, the RD complex can be purified by an ordinary method. For example, in the case where the polypeptide chain has a tag sequence such as FLAG$^{(R)}$ sequence and poly His sequence, a publically-known purification method can be applied depending on the sequence. Before the modifying reagent is reacted, the RD complex may be bound to a carrier having a specific antibody against a tag sequence on the basis affinity binding. Since such an affinity binding is not cleaved during the reaction of the modifying reagent, the RD complex may be purified after the modifying reagent is reacted by using the affinity binding.

The RD complex produced by one or more embodiments of the above-described method comprises a polypeptide chain, an mRNA molecule and a ribosome, 1 or more reactive amino acid residues selected from the group consisting of a cysteine residue, a lysine residue, a histidine residue and a tryptophan residue in the polypeptide chain is modified by the used modifying reagent, and the mRNA molecule comprises a base sequence encoding the amino acid sequence of the polypeptide chain. The RD complex can be distinguished from an unmodified RD complex, since the RD complex has a structure in which the group 'A' in the above-described formulae (1), (1a) to (1e) is replaced by the group 'Ax' due to the reaction, wherein 'Ax' is a binding group formed by reacting a side chain of the cysteine residue, the lysine residue, the histidine residue or the tryptophan residue.

The present application claims the benefit of the priority date of Japanese patent application No. 2016-113935 filed on Jun. 7, 2016. All of the contents of the Japanese patent application No. 2016-113935 filed on Jun. 7, 2016, are incorporated by reference herein.

EXAMPLES

Hereinafter, one or more embodiments of the present invention are described in more detail with Examples. The present invention is, however, not restricted to the following Examples in any way, and additional appropriate changes may be made, which are within the range of the above descriptions and the following descriptions. Such a modified embodiment, is also included in the technical scope of the present invention.

Example 1

(1) Preparation of RNA Library

In this section (1), a method for preparing an RNA library which contained $10^{12}$ or more RNA having the sequence containing the sequence of $(NNK)_{10}$ [wherein 'N' is A, U, G or C, 'K' is G or U, 'NNK' corresponded to all of codons] by NNK method is described.

In order to prepare the above-described RNA library, the template DNA (base sequence: SEQ ID NO: 1, amino acid sequence: SEQ ID NO: 2) having the structure of FIG. 1 was used. Specifically, 5' fragment was prepared in the PCR cycle described in Table 2 by using a reaction mixture having the composition described in Table 1 and a plasmid as a template DNA. In Table 1, SFFnew_130816 is a forward primer and Ma3frag_R0502 is a reverse primer.

TABLE 1

| | |
|---|---|
| 2× buffer | 150 μL |
| 2 mM dNTPs | 60 μL |
| 10 μM 5FFnew_130816 | 9 μL |
| 10 μM 5Ma3frag_R0502 | 9 μL |
| 50 ng/μL template DNA | 0.5 μL |
| H₂O | 66.5 μL |
| Polymerase ("KOD FX Neo" TOYOBO) | 6 μL |
| Total | 300 μL |

TABLE 2

| | | |
|---|---|---|
| 94° C. | 2 min | |
| 98° C. | 10 sec | ↑ |
| 57° C. | 30 sec | 25 cycles |
| 68° C. | 20 sec | ↓ |
| 4° C. | ∞ | |

Then, 3' fragment of the template DNA was prepared in the PCR cycle described in Table 4 by using the reaction mixture having the composition described in Table 3. In Table 3, Ma10NNK_F0502 is a forward primer and 3F-R is a reverse primer.

TABLE 3

| | |
|---|---|
| 2× buffer | 150 μL |
| 2 mN dNTPs | 60 μL |
| 10 μM Ma10NNK_F0502 | 9 μL |
| 10 μM 3F-R | 9 μL |
| 50 ng/μL template DNA | 0.5 μL |
| H₂O | 66.5 μL |
| Polymerase ("KOD FX Neo" TOYOBO) | 6 μL |
| Total | 300 μL |

TABLE 4

| | | |
|---|---|---|
| 94° C. | 2 min | |
| 98° C. | 10 sec | ↑ |
| 57° C. | 30 sec | 25 cycles |
| 68° C. | 40 sec | ↓ |
| 4° C. | ∞ | |

Then, the reaction mixture having the composition described in Table 5 was used, overlapping PCR was performed in the PCR cycle described in Table 6, the above-described 5' fragment and 3' fragment were linked, and the template DNA was obtained by amplification of the entire length. In Table 5, X to Z indicate that 1×10¹² of 5' fragment and 3' fragment were used, and the total amount of the reaction mixture was adjusted to 60 μL by adding water.

TABLE 5

| | |
|---|---|
| 2× buffer | 3 μL |
| 2 mM dNTPs | 12 μL |
| 10 μM 5FFnew_130816 | 0.9 μL |
| 10 μM 3F-R | 0.9 μL |
| H₂O | Z μL |
| Polymerase ("KOD FX Neo" TOYOBO) | 6 μL |
| 5' fragment | X μL |
| 3' fragment | Y μL |
| Total | 60 μL |

TABLE 6

| | | |
|---|---|---|
| 94° C. | 2 min | |
| 98° C. | 10 sec | ↑ |
| 57° C. | 30 sec | 15 cycles |
| 68° C. | 20 sec | ↓ |
| 4° C. | ∞ | |

The obtained above-described template DNA was used as a template, and the reaction mixture having the composition described in Table 7 was subjected to a reaction at 37° C. for 5 hours to obtain an RNA library containing 10¹² or more mRNA having the base sequence of SEQ ID NO: 3. The mRNA contained in the library had FLAG$^{(R)}$ site, His6 site, a random sequence, TEV protease site and a spacer sequence in this order from the 5' side as described in FIG. 1 and did not have a stop codon.

TABLE 7

| | |
|---|---|
| 10× buffer | 10 μL |
| 50 mM DTT | 10 μL |
| 10 mM NTP Mixture | 20 μL |
| Template DNA | 8 μL |
| H₂O | 19.5 μL |
| T7 RNA polymerase | 2.5 μL |
| Total | 50 μL |

(2) Preparation of Ribosome Display Complex Library

A ribosome display (RD) complex was prepared from the above-described RNA library by using a reconstituted cell-free protein synthesis kit ("PURE frex$^{(R)}$" manufactured by GeneFrontier). Separately, 5 μL of streptavidin-magnetic particle ("NanoLink™ Streptavidin Magnetic Beads" manufactured by Solulink) was diluted to 150 μL. The RD complex reaction mixture and anti-FLAG$^{(R)}$ M2 antibody-binding agarose beads (manufactured by Sigma-Aldrich, 20 μL) were mixed, and the mixture was stirred at 4° C. for 60 minutes. The anti-FLAG$^{(R)}$ M2 antibody-binding agarose beads to which the RD complex having FLAG sequence in the peptide part was bound was collected.

(3) Cyclization Reaction of Peptide

After the collected agarose beads were diluted to 80 μL, 10 mM tris (2-carboxyethyl) phosphine hydrochloride (4 μL) at a final concentration of 0.5 mM as a reducing agent and 40 mM 1,3-dibromo-2-propanone (4 μL) at a final concentration of 2 mM as a modifying reagent were added thereto. The mixture was subjected to a cyclization reaction at 4° C. for 3 hours. It is not necessary to add a reducing agent for the reaction. After the cyclization reaction, the RD complex was separated from the agarose beads by adding FLAG peptide.

(4) Selection of HSP90 Affinity Peptide

Separately, a heat shock protein HSP90 to which biotin was bound was mixed with the above-described streptavidin-magnetic particle diluted liquid (5 μL) in a molar ratio of 1:1, and the mixture was stirred at 4° C. to bind HSP90 on the magnetic particle. For a comparison, a magnetic particle dispersion was prepared except that HSP90 was not bound.

The solution of the RD complex having the cyclized peptide obtained in the above (3) and the magnetic particle dispersion were mixed, and the mixture was stirred at 4° C. for 1 hour. The magnetic particle was collected by using a magnetic stand, and the RNA was dissociated from the RD complex which bound to HSP90 on the magnetic particle by adding 0.05 M EDTA. After the magnetic particle was removed by using a magnetic stand, RNA was purified by using RNA concentration/purification kit ("RNeasy Min-Elute Cleanup Kit" manufactured by QIAGEN). Then, the RNA was subjected to a reaction in the composition described in Table 8 at 65° C. for 5 minutes, and then the reaction mixture was subjected to a reaction in the composition described in Table 9 at 50° C. for 1 hour and further at 70° C. for 15 minutes for reverse transcription.

TABLE 8

| | |
|---|---|
| 10 μM middleR_140407 | 0.3 μL |
| 2 mM dNTPs | 7.5 μL |
| H$_2$O | 3.7 μL |
| RNA | 8 μL |
| Total | 19.5 μL |

TABLE 9

| | |
|---|---|
| 5× First Stand Buffer | 6 μL |
| 50 mM DTT | 1.5 μL |
| H$_2$O | 1.5 μL |
| Reverse transcriptase ("Superscript III RT" Thermo Fisher Scientific) | 1.5 μL |
| The above reaction mixture | 19.5 μL |
| Total | 30 μL |

The cDNA obtained by the above-described reverse transcription reaction was subjected to RT-PCR to amplify the sequence containing a random sequence. Specifically, the reaction mixture having the composition described in Table 10 was used, and PCR was performed by the PCR cycle described in Table 11.

TABLE 10

| | |
|---|---|
| 10× buffer | 5 μL |
| 2 mM dNTPs | 5 μL |
| 25 mM MgSO$_4$ | 2 μL |
| 10 μM MamiddleR_F0502 (SEQ ID NO: 4) | 1.5 μL |
| 10 μM middleR_140407 (SEQ ID NO: 5) | 1.5 μL |
| cDNA | 5 μL |
| H$_2$O | 29 μL |
| DNA polymerase ("KOD Plus Ver.2" TOYOBO) | 1 μL |
| Total | 50 μL |

TABLE 11

| | | |
|---|---|---|
| 94° C. | 2 min | |
| 98° C. | 10 sec | ↑ |
| 57° C. | 30 sec | 40 cycles |
| 68° C. | 20 sec | ↓ |
| 4° C. | ∞ | |

Separately, 5' fragment (SEQ ID NO: 6) was prepared similarly to the above-described (1) except that the heating time at 68° C. in the PCR cycle was changed to 15 seconds, and 3' fragment (SEQ ID NO: 7) was prepared similarly except, that 3fragF_140407 was used as a forward primer and the heating time at 68° C. in the PCR cycle was changed to 25 seconds. Then, each fragment was connected by overlapping PCR and the obtained DNA was amplified similarly except that a solution containing the cDNA having the above-described random sequence in addition to the obtained 5' fragment and 3' fragment was used and the amount of polymerase was changed to 0.6 μL.

Figure 2:
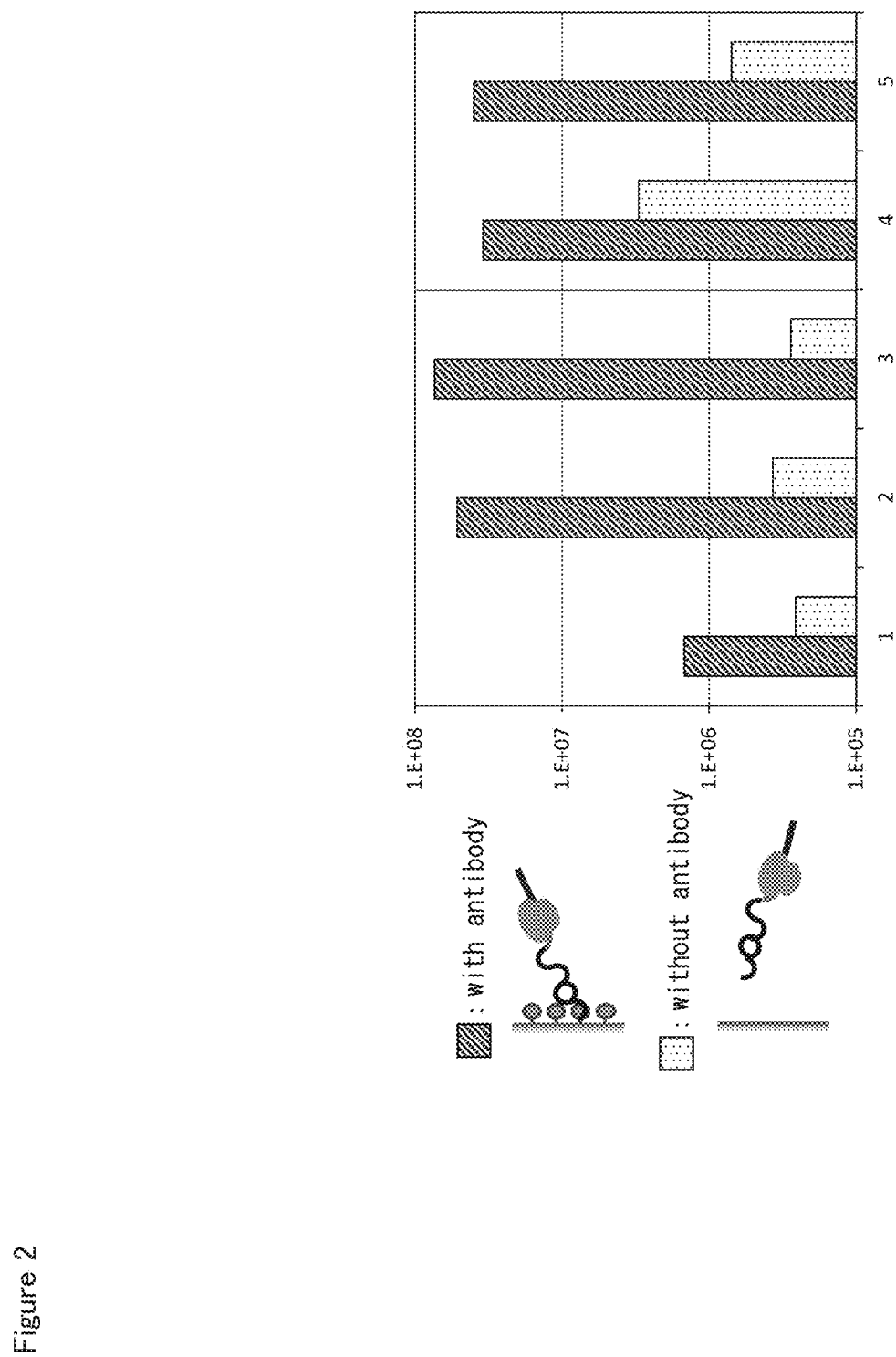
FIG. 2 is a graph to demonstrate the measurement result of the amounts of the ribosome display complex bound to a magnetic particle on which HSP90 was bound and a magnetic particle on which HSP90 was not bound.

The mRNA was transcribed similarly to the above-described (1) by using the obtained DNA. The mRNA was used in the above described Step (2) of "preparing ribosome display complex library", and the RD complex having an affinity for HSP90 was collected similarly to the above. The above-described procedure was repeated until it was confirmed that the amount of the mRNA contained in the RD complex which bound to HSP90 was not increased. Hereinafter, one-time iteration is referred to as "Round". In Rounds 1 to 3, the molar ratio of the RD complex and the used HSP90 as RD complex: HSP90 was adjusted to 3:1. In Rounds 4 and 5, the molar ratio was adjusted to 10:1. The result is shown in FIG. 2 with the amount of mRNA before being contacted with HSP90 and the amount of mRNA without using HSP90. As the result shown in FIG. 2, the amount of the RD complex which bound to HSP90 was increased in Round 2 in comparison with Round 1. On the one hand, after Round 2, since such an increase could not be found, the concentration of the RD complex having an affinity for HSP90 was considered to be completed.

(5) Identification of Peptide Having Affinity for HSP90

By PCR using the entire length DNA as a template in the Round in which it was confirmed that the sequence was concentrated and Taq polymerase, 'A' was added to the end. This protruding end and a cloning kit ("pGEM T Easy Cloning Kit" manufactured by Promega) were used to ligate to the attached plasmid DNA. JM109 competent cell was transformed by using the obtained plasmid and cultivated. By using the plasmid of each clone extracted from the colony formed by the cultivation, the amino acid sequence of the entire length chain DNA was analyzed. Among the obtained amino acid sequences, the sequences of the random, part (NNK part) are shown in Table 12.

TABLE 12

| Sequence symbol | Sequence |
|---|---|
| a | CWVFLRGRWSPC |
| b | CWVFLRGRWLRC |
| c | CWVFLRGKWAVC |
| d | CWVFLRGTWYGC |
| e | CWVFLRGSWSLC |
| f | CWVFLRGSWYPC |
| g | CWVFLRGGWFVC |
| h | CWVFLRGEWRVC |
| i | CWVFLRGMWMQC |
| j | CWVFLRGLWRAC |
| k | CWVFLRGVWLSC |
| l | CRWVFLRGNWLC |
| m | CRWVFLRGRVWC |
| n | CVWVFLRGRVWC |

TABLE 12-continued

| Sequence symbol | Sequence |
|---|---|
| o | CTWVFLRGRVWC |
| p | CSWVFLRGVMYC |

As shown in Table 12, it was found that up to 16 kinds of mRNA which encodes the peptides having an affinity for HSP90 can be selected from the library containing $10^{12}$ or more mRNA by one or more embodiments of the screening method and the amino acid, sequences of the selected peptides are similar.

(6) Confirmation of Binding Ability of Obtained Sequence

Figure 3:
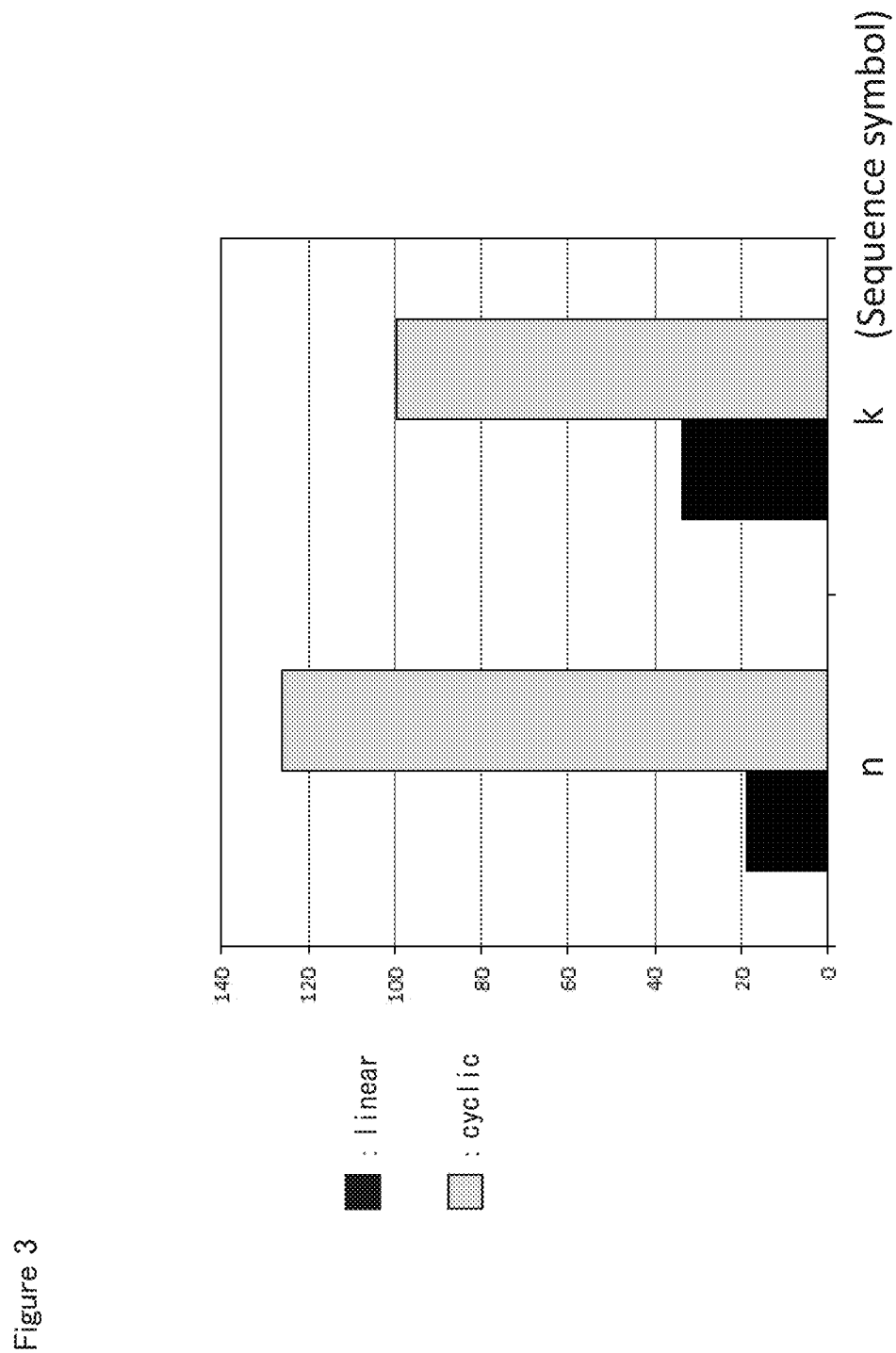
FIG. 3 is a graph to demonstrate the measurement result of the affinities of the ribosome display complex of which polypeptide chain was modified and the ribosome display complex of which polypeptide chain was not modified for HSP90.

An affinity of each clone obtained in the above-described (5) for HSP90 was evaluated. Specifically, RNA was synthesized by using the entire length DNA of each clone synthesized in the above-described (5) as a template similarly to the above-described (1), and ribosome display complexes were prepared similarly to the above-described (2). In addition, a part of the polypeptides were cyclized similarly to the above-described (3). The affinity of the obtained each ribosome display complex for HSP90 was evaluated similarly to the above-described (4). The affinity of each clone for HSP90 was determined by measuring an amount of the collected complex. The result is shown in FIG. 3. The alphabet in FIG. 3 corresponds to the sequence symbol in the above-described Table 12.

As the result shown in FIG. 3, among the ribosome display complexes of which affinity for HSP90 was evaluated, 3 kinds of polypeptides have an affinity for HSP90. It was suggested that 2 kinds among the polypeptides can bind 10 times stronger in the cyclized state linked by a modifying reagent. It was demonstrated from the results that a modifying reagent can be linked to the polypeptide displayed on a RD complex with maintaining the function of the RD complex. In addition, a clone having about 6 times affinity can be obtained depending on with or without a modifying reagent. In other words, it was suggested that an affinity for HSP90 can be improved by cyclizing a polypeptide and a modifying reagent is useful for connection.

Example 2

Cyclization Reaction of Peptide

Figure 4:
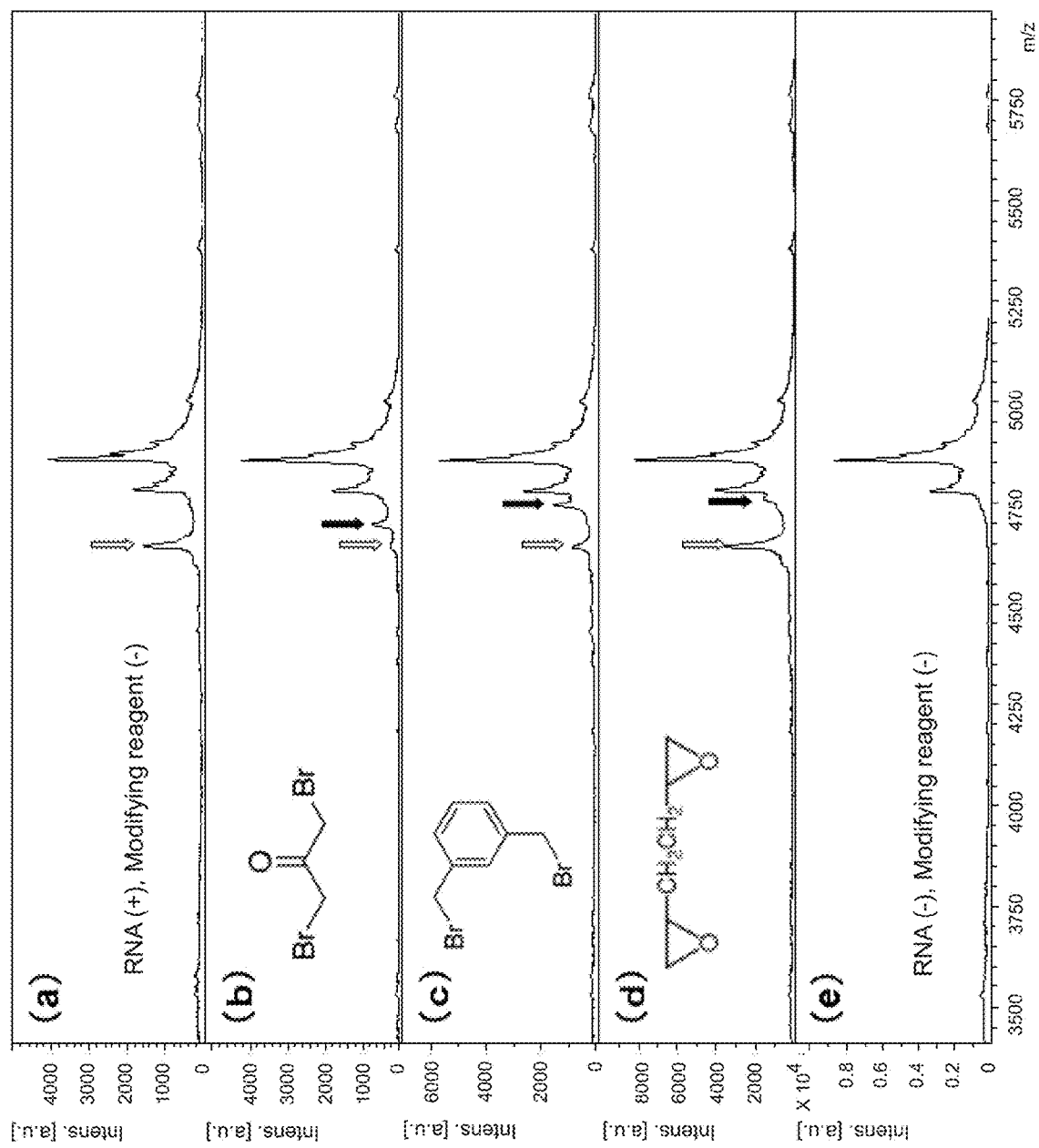
FIG. 4 is a mass spectrum of the ribosome display complex with which various modifying reagents were reacted.

A RD complex was prepared by using a reconstituted cell-free protein synthesis kit ("PURE frex(R)" manufactured by GeneFrontier) and mixing $2.5 \times 10^{13}$ RNA (SEQ ID NO: 8) molecules having FLAG sequence, His6 sequence and a base sequence which encoded TEV protease site for a reaction at 37° C. for 35 minutes, and an anti-FLAG(R) M2 antibody-binding agarose beads manufactured by Sigma-Aldrich (2 µL) was added to the reaction mixture in order to be bound to the RD complex. Further, tris(2-carboxyethyl) sodium salt (pH 7, final concentration: 0.5 mM) as a reducing agent and each modifying reagent shown in FIG. 4 at the final concentration of 2 mM were added, and the mixture was stirred at 4° C. for 3 hours to cyclize the peptide in the RD complex on the beads. After the reaction, the RD complex was liberated from the beads by adding FLAG peptide (sequence: DYKDDDDK, 5 mg). The beads were separated from the reaction mixture to be removed, and the complex was dissociated by adding phosphate buffered saline without $Mg^{2+}$ (pH 7.5, 100 µL). Then, the peptide chain was purified by using His-tag beads. After the purified polypeptide was cleaved by TEV protease, the molecular weight of the peptide fragment (SEQ ID NO: 9) which contained the cyclized part and of which N-terminal was formylated was measured by MALDI-TOFMS. The chemical structure of the modifying reagent and the obtained mass spectrum are shown in FIG. 4. In FIG. 4, (a) is a mass spectrum of the reaction mixture without adding a modifying reagent, and (e) is a mass spectrum of the reaction mixture which was similarly reacted except that RNA was not used and corresponds to a background signal. In addition, a white arrow indicates a peak of uncyclized peptide chain and a black arrow indicates a peak of cyclized peptide chain.

As the result shown in FIG. 4, it was found that (b) when 1,3-dibromo-2-propanone is used and (c) when 1,3-bis(bromomethyl)benzene is used, a cyclization reaction proceeds. Since a reaction efficiency is relatively low but a cyclized compound can be confirmed (d) when 1,5-hexazine diepoxide is used as a modifying reagent, an epoxide can be used as a cyclizing reagent.

In each mass spectrum, a peak of molecular weight increased by one molecule of the used modifying reagent can be clearly identified but a peak of molecular weight increased by two molecules of the used modifying reagent cannot be clearly recognized. It is considered from the result that only one molecule of a modifying reagent binds to the polypeptide chain.

Example 3

Cyclization Reaction of Peptide

Figure 5:
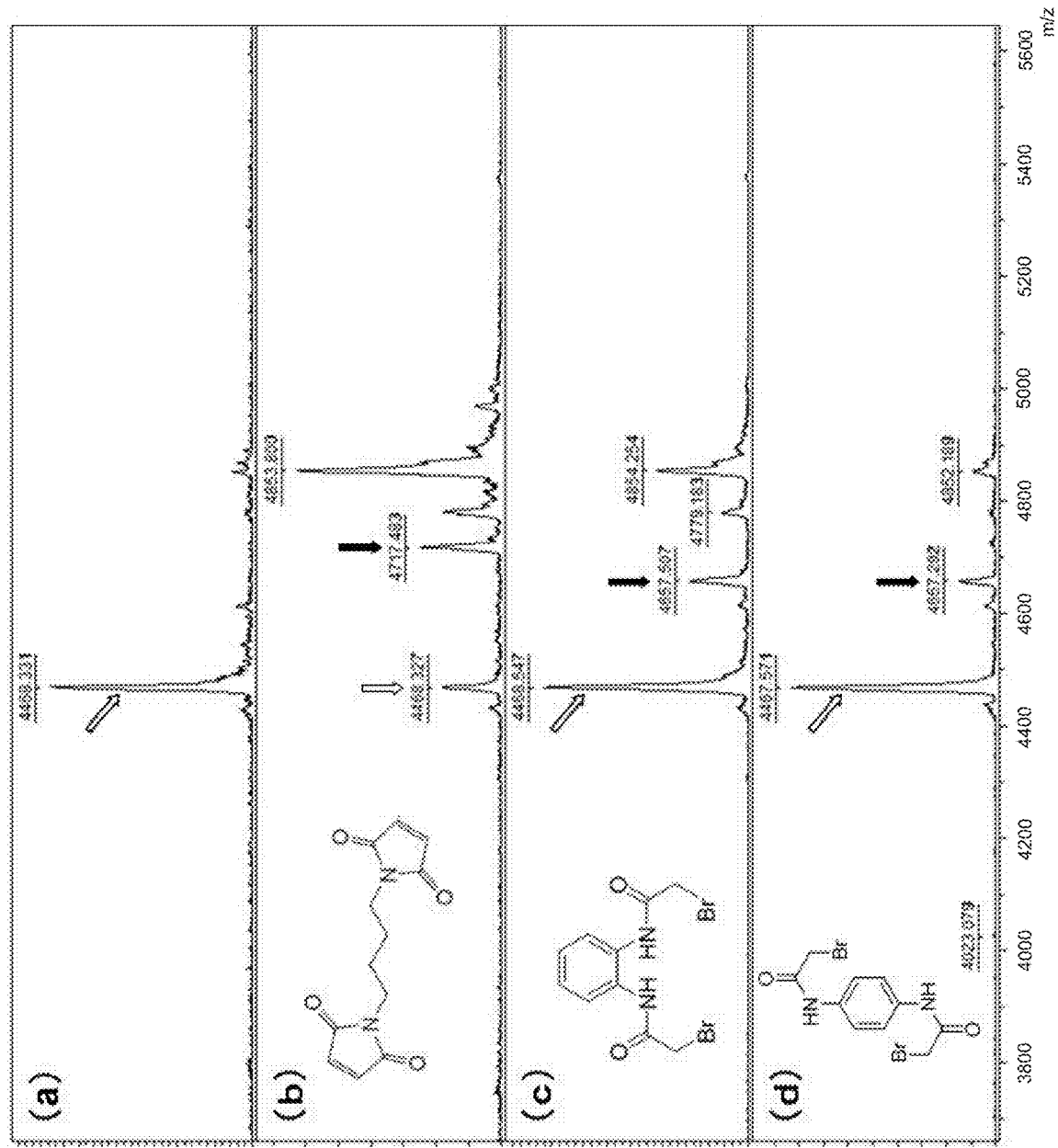
FIG. 5 is a mass spectrum of the ribosome display complex with which various modifying reagents were reacted.

A cyclization reaction was performed similarly to the above-described Example 2 except that RNA having the base sequence of SEQ ID NO: 10 was used and the modifying reagent shown in FIG. 5 was used. The result is shown in FIG. 5.

It was found as FIG. 5 that both of a maleimide-type modifying reagent (FIG. 5, (b)) and a haloacetylamino-type modifying reagent (FIG. 5, (c) and (d)) can be used as a cyclizing reagent.

In this experiment, it was found that a peak of molecular weight increased by one molecule of the used modifying reagent can be clearly identified. In addition, other peak was also recognized but the molecule thereof was different from the calculated molecular weight of a RD complex to which 2 or more modifying reagents were bound; therefore, the peak is considered to be derived from a ribosomal protein which cannot be removed by the protease treatment. It was thought from the result that only one modifying reagent was bound to the polypeptide chain.

Example 4

Cyclization Reaction of Peptide

A cyclization reaction was performed similarly to the above-described Example 2 except that the RNA having the base sequence of SEQ ID NO: 11 was used, disuccinimidyl suberate was used as a modifying reagent, and the pH of the reaction mixture was changed to 7.4, 7.7 or 8.0. The result in the case where the pH of the reaction mixture was 7.4 is shown in FIG. 6, the result in the case where the pH was 7.7 is shown in FIG. 7, and the result in the case where the pH was 8.0 is shown in FIG. 8.

Figure 6:
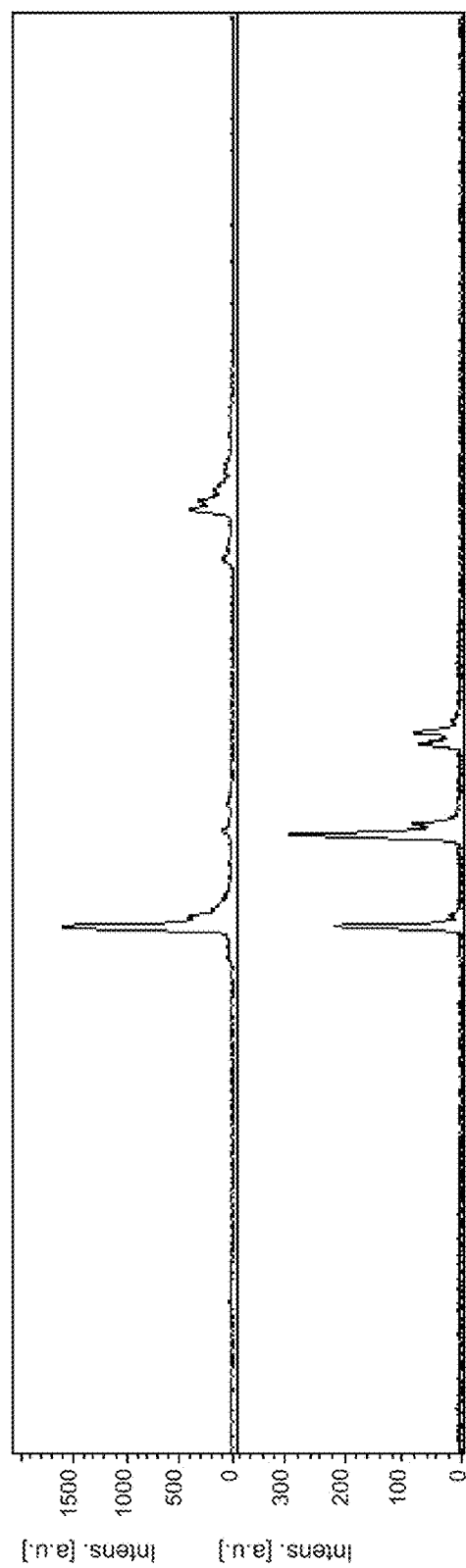
FIG. 6 is a mass spectrum in the case where the ribosome display complex was subjected to a cyclization reaction at pH 7.4.
Figure 7:
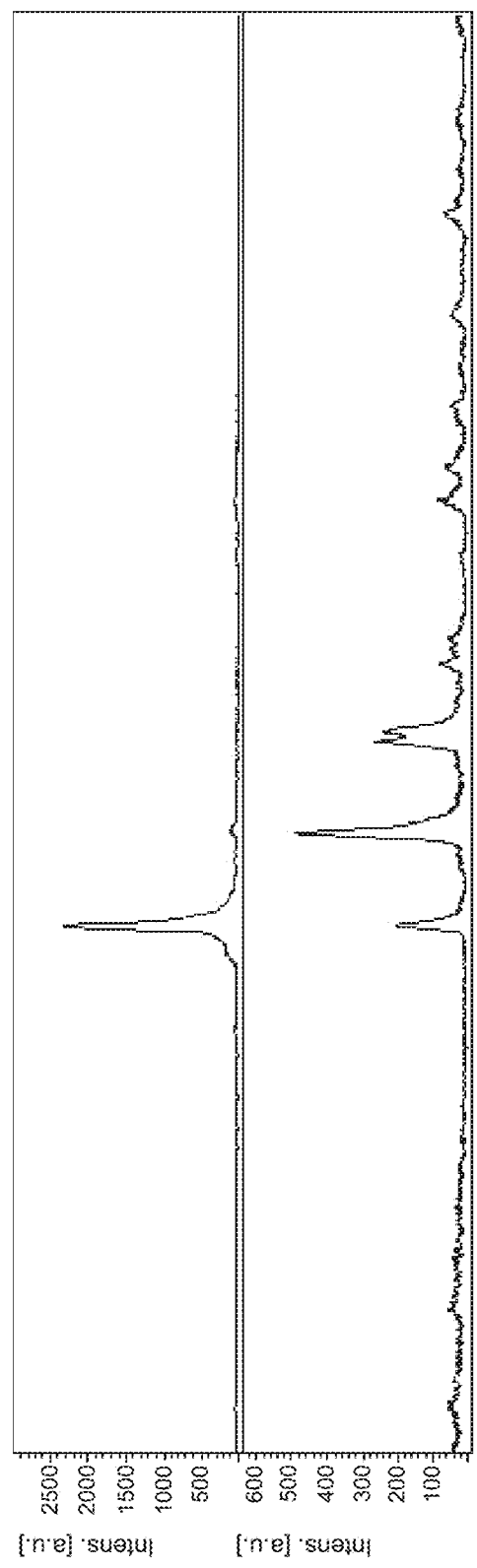
FIG. 7 is a mass spectrum in the case where the ribosome display complex was subjected to a cyclization reaction at pH 7.7.
Figure 8:
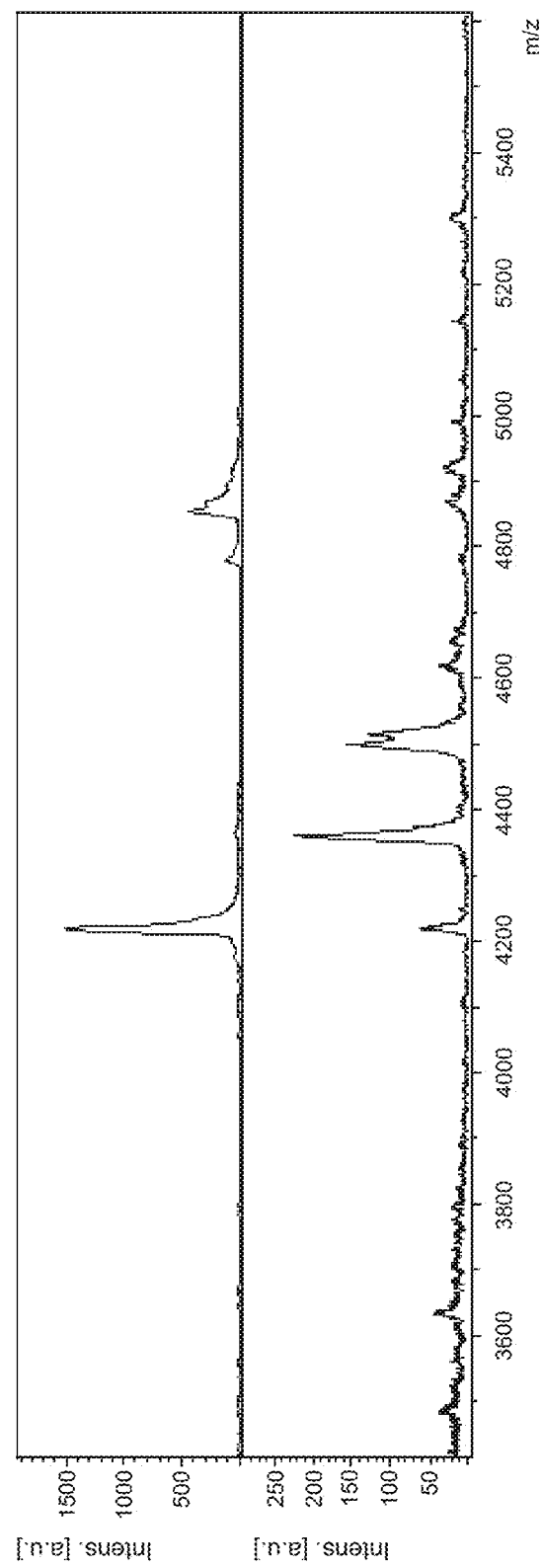
FIG. 8 is a mass spectrum in the case where the ribosome display complex was subjected to a cyclization reaction at pH 8.0.

As FIGS. 6 to 8, the reaction can be proceeded under any pH conditions. In addition, it was suggested that since the strength of a peak of the compound to which, one more modifying reagent, totally 2 molecules, is bound becomes stronger when the pH is higher, the modifying reagent is also bound to a basic amino acid such as histidine and tryptophan.

On the one hand, since a peak of the RD complex to which 3 or more modifying reagents were bound could not be clearly recognized, it was thought that one molecule or two molecules of a modifying reagent bound to the polypeptide chain also in this experiment.

Example 5

Cyclization Reaction of Peptide

A cyclization reaction was performed similarly to the above-described Example 2 except that the RNA encoding the amino acid sequence of SEQ ID NOs: 12 to 14 and disuccinimidyl suberate as a modifying reagent were used. The result of the amino acid sequence of SEQ ID NO: 12 is shown in FIG. 9, the result of the amino acid sequence of SEQ ID NO: 13 is shown in FIG. 10, and the result of the amino acid sequence of SEQ ID NO: 14 is shown in FIG. 11.

Figure 9:
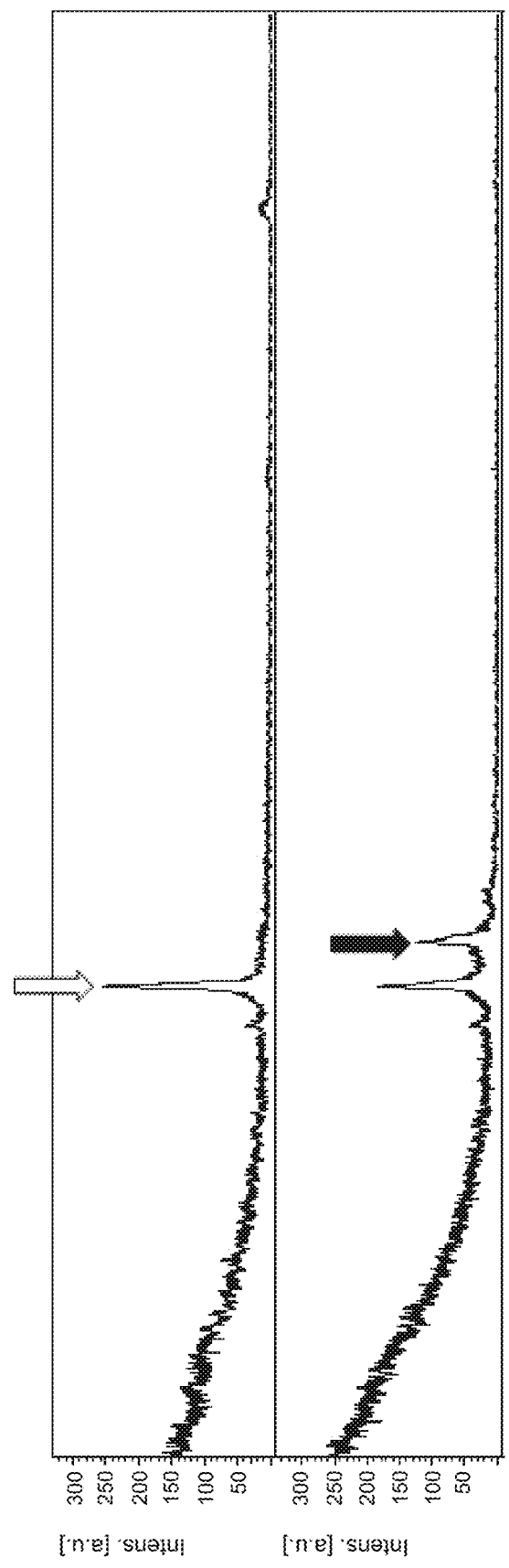
FIG. 9 is a mass spectrum in the case where the ribosome display complex having the amino acid sequence of SEQ ID NO: 12 was cyclized by disuccinimidyl suberate.
Figure 10:
FIG. 10 is a mass spectrum in the case where the ribosome display complex having the amino acid sequence of SEQ ID NO: 13 was cyclized by disuccinimidyl suberate.
Figure 11:
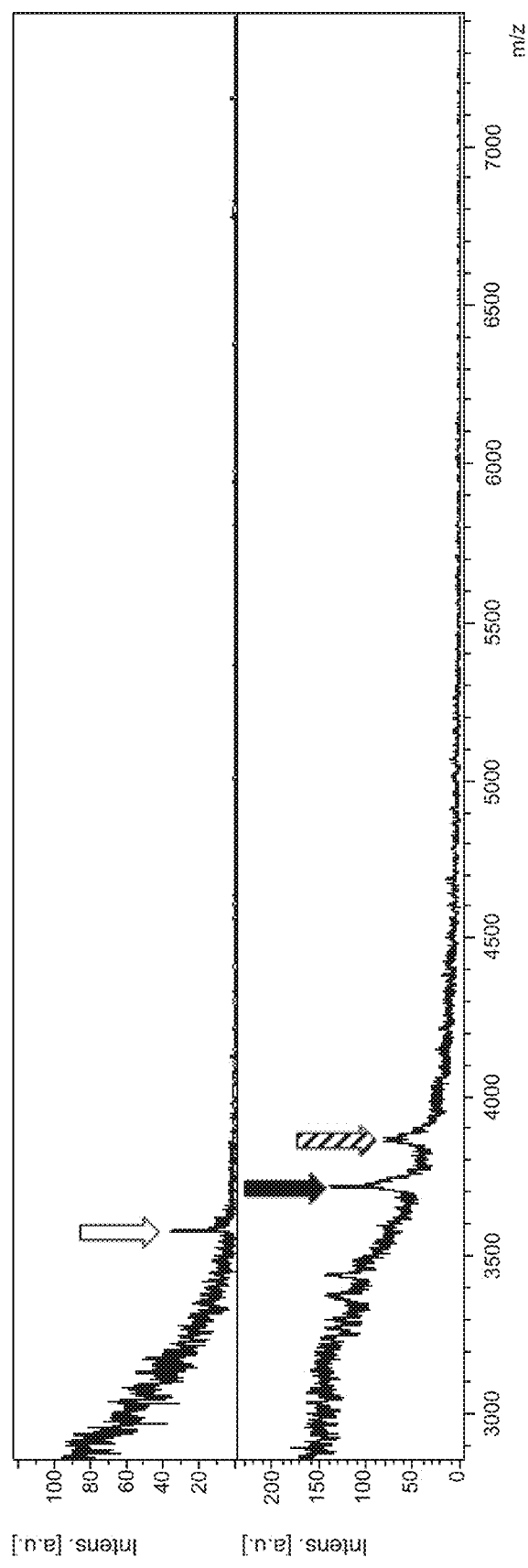
FIG. 11 is a mass spectrum in the case where the ribosome display complex having the amino acid sequence of SEQ ID NO: 14 was cyclized by disuccinimidyl suberate.

As FIGS. 9 to 11, it was suggested that a disuccinimidyl compound having 2 activated carboxy groups can react with 2 lysine side chain amino groups to cyclize the peptide and further react with a secondary amino acid of histidine side chain.

In addition, it was thought that since the main peak after the reaction is a peak of the RD complex bound by one molecule or two molecules of the modifying reagent also in this experiment, one molecule or two molecules of the modifying reagent bind to the polypeptide chain.

Example 6

Biotinylation Reaction of Peptide

Figure 12:
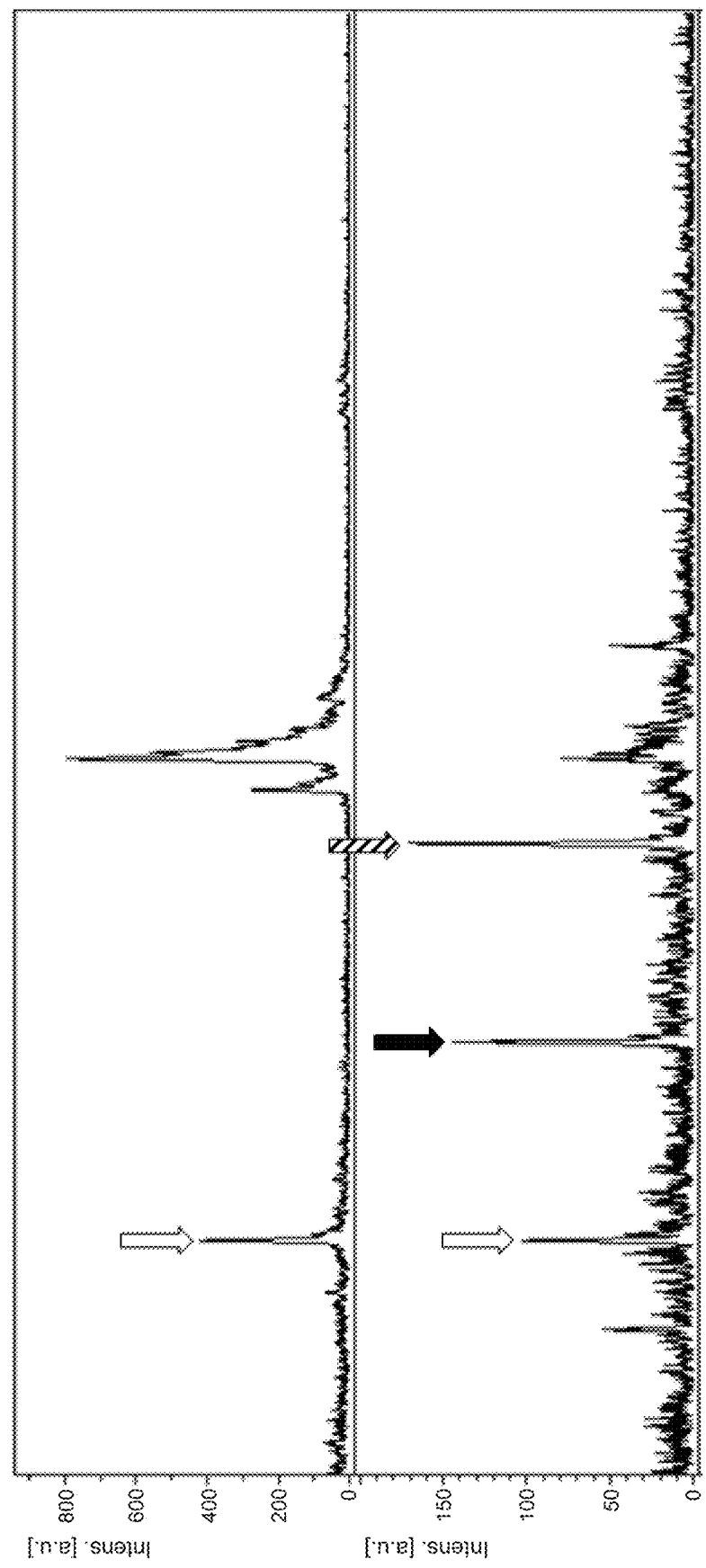
FIG. 12 is a mass spectrum in the case where the ribosome display complex having the amino acid sequence of SEQ ID NO: 13 was modified by EZ-Link NHS-PEG4-Biotin.

The peptide was modified similarly to the above-describe Example 2 except that the RNA encoding the peptide sequence of SEQ ID NO: 13 and EZ-Link NHS-PEG4-Biotin manufactured by Thermo Fisher as a modifying reagent were used. As FIG. 12, a signal to demonstrate biotinylation was recognized. Since this peptide sequence contains 2 lysines, a peptide having 2 biotins was detected (diagonal arrow) in addition to a peptide having 1 biotin (black arrow). Thus, it is thought that one molecule or two molecules of a modifying reagent bind to the polypeptide chain.

Example 7

Cyclization Reaction and Biotinylation Reaction of Peptide

Figure 13:
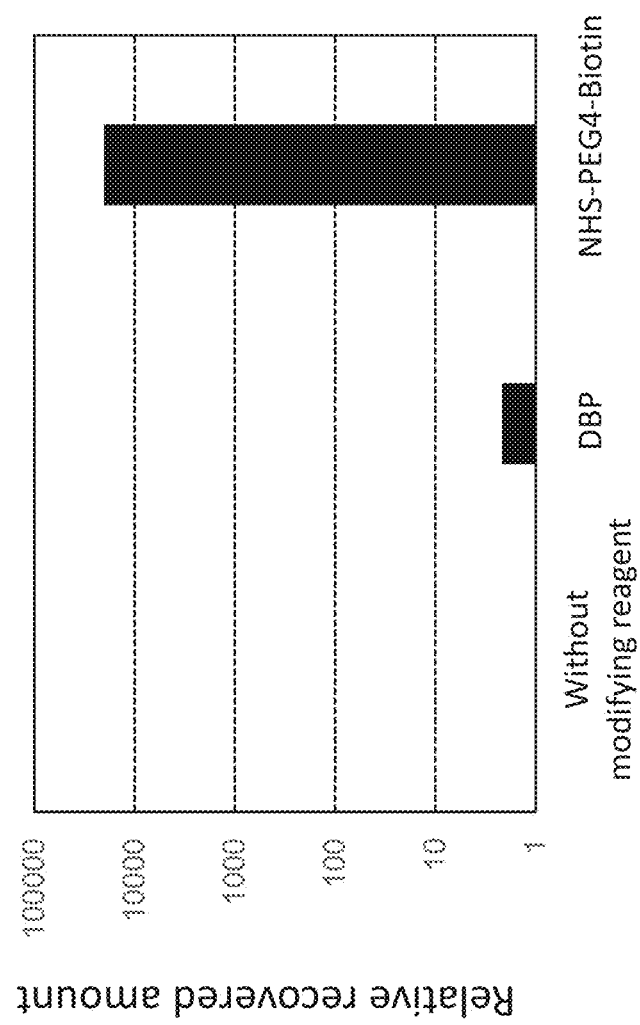
FIG. 13 is a graph to relatively demonstrate the affinities of an unmodified ribosome display complex or the ribosome display complex modified by 1,3-dibromo-2-propanone or EZ-Link NHS-PEG4-Biotin for HSP90.

A biotin-modified RD complex was prepared similarly to the above-described Example 2 except that the RNA encoding the peptide sequence of SEQ ID NO: 12 was used and 1,3-dibromo-2-propanone or EZ-Link NHS-PEG4-Biotin manufactured by Thermo Fisher was used as a modifying reagent. The above-described streptavidin-magnetic particle diluted liquid (5 µL) was added to the biotinylated complex to collect the magnetic particle by using a magnetic stand. The RNA was dissociated from the RD complex bound to HSP90 on the magnetic particle by adding 0.05 M EDTA to the collected magnetic particle. After the magnetic particle was removed by using a magnetic stand, the RNA was purified by using RNA concentration/purification kit ("RNeasy MinElute Cleanup Kit" manufactured by QIAGEN). An amount of the recovered RNA in the case of the modification by each modifying reagent was measured by quantitative RT-PCR and relatively compared by using an amount of the recovered RNA without a modifying reagent as a back ground. The result, is shown in FIG. 13. As the result shown in FIG. 13, it was suggested that the RD complex was biotinylated by NHS-PEG4-Biotin and RNA could be recovered.

Example 8

Comparison of Modification Condition (1) Condition 1

A reconstituted cell-free protein synthesis kit ("PURE frex$^{(R)}$" manufactured by GeneFrontier) was used, and tris (2-carboxyethyl) sodium salt (pH 7, final concentration: 0.5 mM) as a reducing agent and 1,3-dibromo-2-propanone as a modifying reagent at a final concentration of 2 mM were added to 50 µL of a reaction mixture containing a ribosome for a reaction at 4° C. for 3 hours. Then, factors in the above-described reconstituted cell-free protein synthesis kit except that a ribosome in an amount needed for 50 µL of a reaction mixture and 2.5×10$^{12}$ molecules of RNA (SEQ ID NO: 8) were added thereto, and the mixture was reacted at 37° C. for 35 minutes to prepare a RD complex. Into the reaction mixture, anti-FLAG$^{(R)}$ M2 antibody-binding agarose beads (manufactured by Sigma-Aldrich, 2 µL) were added to bind the RD complex to the beads. The mixture was stirred at 4° C. for 3 hours without further adding anything. After stirring, the RD complex was dissociated from the beads by adding FLAG peptide (sequence: DYKDDDDK, 5 mg). An amount of the obtained RD complex was measured by quantitative RT-PCR. The result is shown in FIG. 14.

(2) Condition 2

In Condition 2, after a RD complex was prepared, a modifying reagent was reacted similarly to the above-described Example. Specifically, the above-described reconstituted cell-free protein synthesis kit was used, and 50 µL of a reaction mixture containing a ribosome was incubated at 4° C. for 3 hours without adding a modifying reagent. Then, a RD complex was prepared similarly to Condition 1, and anti-FLAG$^{(R)}$ M2 antibody-binding agarose beads (manufactured by Sigma-Aldrich, 2 µL) were added to the reaction mixture to bind the RD complex to the beads. Further, tris(2-carboxyethyl) sodium salt (pH 7, final concentration: 0.5 mM) as a reducing agent and 1,3-dibromo-2-propanone as a modifying reagent at a final concentration of 2 mM were added, and the mixture was stirred at 4° C. for 3 hours to modify the RD complex on the beads. An amount of the added 1,3-dibromo-2-propanone as a modifying reagent was 1,000,000 times by mole to 1 mole of the RD complex. After the reaction, the RD complex was dissociated from the beads by adding FLAG peptide (sequence: DYKDDDDK, 5 mg). An amount of the obtained RD complex was measured by quantitative RT-PCR. The result is shown in FIG. 14.

Figure 14:
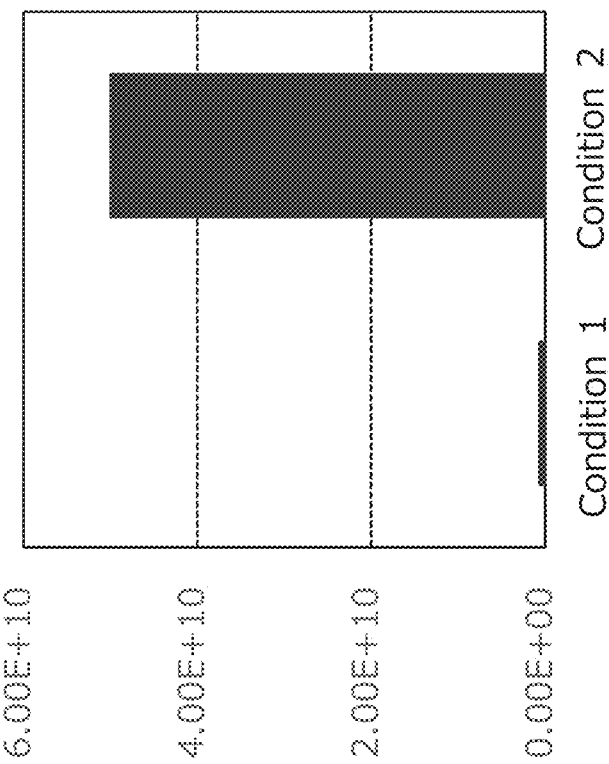
FIG. 14 is a graph to compare the amounts of the ribosome display complexes prepared with changing the timing of addition of a modifying reagent.

As the result shown in FIG. 14, a RD complex could not obtained by treating a ribosome with a modifying agent and then trying to prepare a RD complex. On the one hand, it was found that if a RD complex is treated by a modifying reagent, the obtained RD complex would not be decomposed. In addition, from the results of the above-described Examples, a modifying reagent is considered to react with at least a peptide in a RD complex.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A method for producing a ribosome display complex, comprising:

obtaining a ribosome complex comprising an unmodified polypeptide chain, an mRNA molecule and a ribosome by initiating translation of the mRNA molecule in a cell-free peptide synthesis system comprising the ribosome; and modifying the unmodified polypeptide chain by reacting a side chain reactive functional group in the unmodified polypeptide chain with a modifying reagent to produce the ribosome display complex comprising a modified polypeptide chain, the mRNA molecule and the ribosome, wherein the unmodified polypeptide chain comprises at least one reactive amino acid residue selected from the group consisting of a cysteine residue, a lysine residue, a histidine residue and a tryptophan residue, wherein the at least one reactive amino acid residue comprises the side chain reactive functional group, and wherein the mRNA molecule comprises a base sequence encoding an amino acid sequence of the polypeptide chain, wherein the modifying reagent is a compound represented by the following formula:

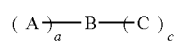

wherein A is a group capable of forming a linkage by reacting with a side chain of the cysteine residue, the lysine residue, the histidine residue or the tryptophan residue, B is a linker group or a single bond, C is a functional group, a is an integer of 1 or more, c is 0 or an integer of 1 or more, provided that when a is an integer of 2 or more, a plurality of A are the same as or different from each other.

2. The method according to claim 1, wherein A is a halogenated alkyl group, an activated carbonyl group, an unsaturated hydrocarbon group, an epoxy group, a sulfonyl-containing group, an isocyanate group, an isothiocyanate group, a carbene-precursor group, a carbene-containing group, a disulfide bond-containing group or a thiol group.

3. The method according to claim 1, wherein
B is the linker group and has one or more selected from the group consisting of: a hetero atom-containing polar group;
a chained or cyclic aliphatic hydrocarbon group optionally having the hetero atom-containing polar group between carbon atoms and optionally having a substituent group; and
an aromatic ring optionally having a substituent group, the hetero atom-containing polar group is —O—, —S—, —NR$_1$—, —CO—, —COO—, —CONR$_2$—, —N=N— or —SO$_2$—,
wherein R1 is a hydrogen atom, a hydrocarbon group or an atomic bonding at a terminal of the linker group, and R2 is a hydrogen atom, a hydrocarbon group or an atomic bonding at a terminal of the linker group, the substituent group on the aliphatic hydrocarbon group is a halogeno group, an aryl group, a carboxy group, an alkoxycarbonyl group or a hydroxy group, and
the substituent group on the aromatic ring is a halogeno group, an alkyl group, an aralkyl group, a carboxy group, an alkoxycarbonyl group, a hydroxyalkyl group or a carboxyalkyl group.

4. The method according to claim 3, wherein
the linker group B has -B1- unit, -B2- unit, -B2-B1- unit or -B2-B1-B3- unit,
B1 is a group having one or more selected from the group consisting of the chained or cyclic aliphatic hydrocarbon group and the aromatic ring,
B2 and B3 are each independently the hetero atom-containing polar group, and
B1 or B2 is bound to A.

5. The method according to claim 4, wherein the modifying reagent is any one of compounds represented by the following formulae:

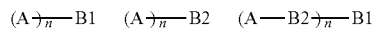

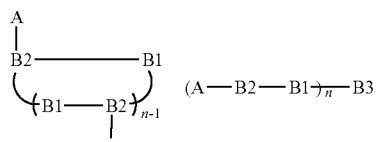

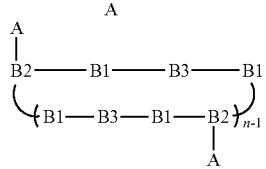

wherein A, B1, B2 and B3 have the same meanings as the above, n is an integer of 1 or more, one or more of B1, B2 and B3 may be bound by one or more functional groups.

6. The method according to claim 1, wherein
A is a halogenated alkyl group, and
a carbon atom bound by a halogeno group in the halogenated alkyl group is a carbon atom at a position of a carbonyl group or a carbon atom directly binding to an aromatic ring.

7. The method according to claim 1, wherein
the unmodified polypeptide chain comprises two or more of the reactive amino acid residues,
a in the formula is an integer of 2 or more, and
the unmodified polypeptide chain and the modifying reagent form a ring by the reaction of the side chain reactive functional group and the modifying reagent.

8. The method according to claim 1, wherein the unmodified polypeptide chain has 100 to 5000 amino acid residues.

9. The method according to claim 1, wherein the reactive amino acid residue is located at a position selected from the group consisting of the 2$^{nd}$ position from the N-terminal to the 30$^{th}$ position from the C-terminal in the unmodified polypeptide chain.

10. The method according to claim 1, wherein the unmodified polypeptide comprises a random sequence having 1 to 30 amino acid residues within a region ranging from the 2$^{nd}$ position from the N-terminal to the 30$^{th}$ position from the C-terminal.

11. The method according to claim 1, wherein the ribosome is originated from *Escherichia coli*.

12. A ribosome display complex,
comprising a polypeptide chain, an mRNA molecule, and a ribosome, wherein
the polypeptide chain comprises at least one reactive amino acid residue selected from the group consisting of a cysteine residue, a lysine residue, a histidine residue and a tryptophan residue,
the at least one reactive amino acid residue comprises a side chain reactive functional group that is modified with a modifying reagent, and
the mRNA molecule comprises a base sequence encoding an amino acid sequence of the polypeptide chain,
wherein the side chain reactive functional group comprises a modification structure represented by the following formula:

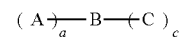

wherein Ax is a binding group formed by reacting the modifying reagent with a side chain of the cysteine residue, the lysine residue, the histidine residue or the tryptophan residue, B is a linker group or a single bond, C is a functional group, a is an integer of 1 or more, c is 0 or an integer of 1 or more, provided that when a is an integer of 2 or more, a plurality of Ax are the same as or different from each other.

13. The ribosome display complex according to claim 12, wherein Ax is a chemical bond formed by reacting a halogenated alkyl group, an activated carbonyl group, an unsaturated hydrocarbon group, an epoxy group, a sulfonyl-containing group, an isocyanate group, an isothiocyanate group, a carbene-precursor group, a carbene-containing group, a disulfide bond-containing group or a thiol group with the side chain of the cysteine residue, the lysine residue, the histidine residue or the tryptophan residue.

14. The ribosome display complex according to claim 13, wherein
B is the linker group and has one or more selected from the group consisting of: a hetero atom-containing polar group; a chained or cyclic aliphatic hydrocarbon group optionally having the hetero atom-containing polar group between carbon atoms and optionally having a substituent group; and an aromatic ring optionally having a substituent group,
the hetero atom-containing polar group is —O—, —S—, —NR$^1$—, —CO—, —COO—, —CONR$^2$—, —N=N— or —SO$_2$—, wherein R$^1$ is a hydrogen atom, a hydrocarbon group or an atomic bonding at a terminal of the linker group, and R$^2$ is a hydrogen atom, a hydrocarbon group or an atomic bonding at a terminal of the linker group,
the substituent group on the aliphatic hydrocarbon group is a halogeno group, an aryl group, a carboxy group, an alkoxycarbonyl group or a hydroxy group, and
the substituent group on the aromatic ring is a halogeno group, an alkyl group, an aralkyl group, a carboxy group, an alkoxycarbonyl group, a hydroxyalkyl group or a carboxyalkyl group.

15. The ribosome display complex according to claim 14, wherein
the linker group B has -B1- unit, -B2- unit, -B2-B1- unit or -B2-B1-B3- unit,
B1 is a group having one or more selected from the group consisting of the chained or cyclic aliphatic hydrocarbon group and the aromatic ring,
B2 and B3 are each independently the hetero atom-containing polar group, and
B1 or B2 is bound to Ax.

16. The ribosome display complex according to claim 12, wherein the side chain reactive functional group comprises a modification structure represented by any one of the following formulae:

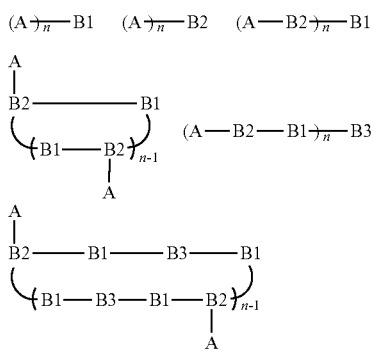

wherein
Ax is a binding group formed by reacting the modifying reagent with a side chain of the cysteine residue, the lysine residue, the histidine residue or the tryptophan residue,
B1 is a group having one or more selected from the group consisting of: a chained or cyclic aliphatic hydrocarbon group optionally having a hetero atom-containing polar group between carbon atoms and optionally having a substituent group; and an aromatic ring optionally having a substituent group,
the hetero atom-containing polar group is —O—, —S—, —NR$^1$—, —CO—, —COO—, —CONR$^2$—, —N=N— or —SO$_2$—, wherein R$^1$ is a hydrogen atom, a hydrocarbon group or an atomic bonding at a terminal of the linker group, and R$^2$ is a hydrogen atom, a hydrocarbon group or an atomic bonding at a terminal of the linker group,
the substituent group on the aliphatic hydrocarbon group is a halogeno group, an aryl group, a carboxy group, an alkoxycarbonyl group or a hydroxy group,
the substituent group on the aromatic ring is a halogeno group, an alkyl group, an aralkyl group, a carboxy group, an alkoxycarbonyl group, a hydroxyalkyl group or a carboxyalkyl group,
B2 and B3 are each independently the hetero atom-containing polar group, B1 or B2 is bound to Ax,
n is an integer of 1 or more,
optionally one or more of B1, B2 and B3 are bound to one or more functional groups.

17. The ribosome display complex according to claim 12, wherein
Ax is a chemical bond formed between a halogenated alkyl group and the side chain of the cysteine residue, the lysine residue, the histidine residue or the tryptophan residue, and
a carbon atom bound by the halogeno group in the halogenated alkyl group is a carbon atom at a position of a carbonyl group or a carbon atom directly binding to an aromatic ring.

18. The ribosome display complex according to claim 12, wherein the polypeptide chain comprises two or more of the reactive amino acid residues,
a in the formula is an integer of 2 or more,
the polypeptide chain and the modification structure form a ring.

19. The ribosome display complex according to claim 12, wherein the polypeptide chain consists of 100 to 5000 amino acid residues.

20. The ribosome display complex according to claim 12, wherein the reactive amino acid residue is located at a position selected from the group consisting of the 2$^{nd}$ position from the N-terminal to the 30$^{th}$ position from the C-terminal in the polypeptide chain.

21. The ribosome display complex according to claim 12, wherein the polypeptide chain comprises a random sequence having 1 to 30 amino acid residues within a region of the 2$^{nd}$ position from the N-terminal to the 30$^{th}$ position from the C-terminal.

22. The ribosome display complex according to claim 12, wherein the ribosome is originated from *Escherichia coli*.

23. The method according to claim 2, wherein if A is a halogenated alkyl group, a is an integer not equal to 3.

24. The method according to claim 5, wherein the functional group is a linker compound to cyclize the polypeptide, a fluorescent dye, a radioactive substance, a drug, a toxin, a nucleic acid, an amino acid, a peptide, a sugar, a lipid, or a polymer.

* * * * *